(12) United States Patent
Sato

(10) Patent No.: US 8,932,228 B2
(45) Date of Patent: Jan. 13, 2015

(54) OPTICAL DEVICE AND BIOLOGICAL INFORMATION DETECTOR

(75) Inventor: Shigemi Sato, Asahi-mura (JP)

(73) Assignee: Seiko Epson Corporation, Tokyo (JP)

( * ) Notice: Subject to any disclaimer, the term of this patent is extended or adjusted under 35 U.S.C. 154(b) by 463 days.

(21) Appl. No.: 13/031,896

(22) Filed: Feb. 22, 2011

(65) Prior Publication Data

US 2011/0237908 A1    Sep. 29, 2011

(30) Foreign Application Priority Data

Mar. 25, 2010   (JP) .................................. 2010-071015

(51) Int. Cl.
| | |
|---|---|
| A61B 5/02 | (2006.01) |
| A61B 5/024 | (2006.01) |
| A61B 5/1455 | (2006.01) |
| A61B 5/00 | (2006.01) |

(52) U.S. Cl.
CPC ......... *A61B 5/02427* (2013.01); *A61B 5/14551* (2013.01); *A61B 5/6898* (2013.01)
USPC ...................................................... 600/502

(58) Field of Classification Search
USPC ................................................. 600/323, 502
See application file for complete search history.

(56) References Cited

U.S. PATENT DOCUMENTS

| | | | | |
|---|---|---|---|---|
| 4,621,643 | A | * | 11/1986 | New et al. ...................... 600/331 |
| 5,553,616 | A | | 9/1996 | Ham et al. |
| 5,995,856 | A | | 11/1999 | Mannheimer et al. |
| 6,041,247 | A | * | 3/2000 | Weckstrom et al. .......... 600/323 |
| 2003/0106987 | A1 | * | 6/2003 | Komaba et al. ............. 250/208.1 |

FOREIGN PATENT DOCUMENTS

| | | |
|---|---|---|
| JP | 2000-116611 A | 4/2000 |
| JP | 2004-337605 A | 12/2004 |
| JP | 2006-269705 A | 10/2006 |

* cited by examiner

*Primary Examiner* — Patricia Mallari
*Assistant Examiner* — Vasuda Ramachandran
(74) *Attorney, Agent, or Firm* — Global IP Conselors, LLP

(57) ABSTRACT

An optical device including a contact part having a contact surface and an opposing surface, the contact surface coming into contact with a test subject and the opposing surface being opposite the contact surface; a support body installed on the opposing surface; a first element supported by the support body; and a second element disposed between the opposing surface and the support body; wherein one of the first element and the second element is a light-emitting element for emitting light towards a detection site of the test subject; another of the first element and the second element is a light-receiving element for receiving reflected light, the reflected light being light emitted by the light-emitting element and reflected at the detection site; and the contact part is formed from a material that is transparent with respect to a wavelength of the light emitted by the light-emitting element.

16 Claims, 16 Drawing Sheets

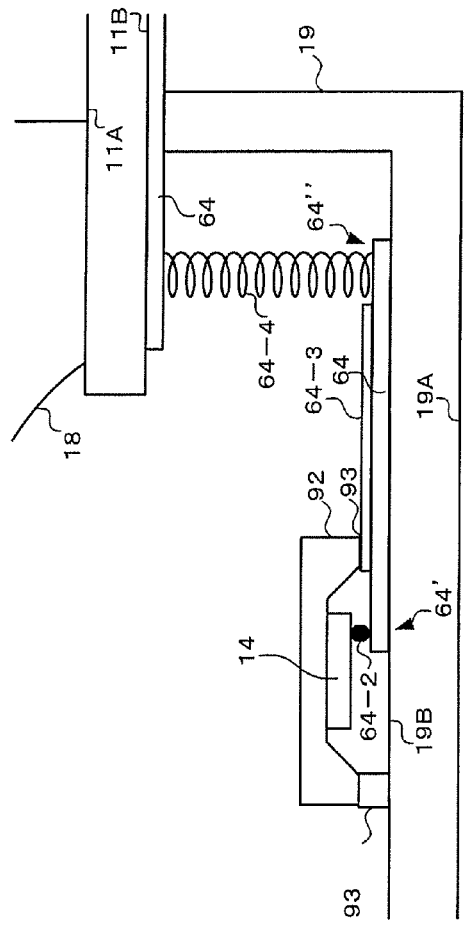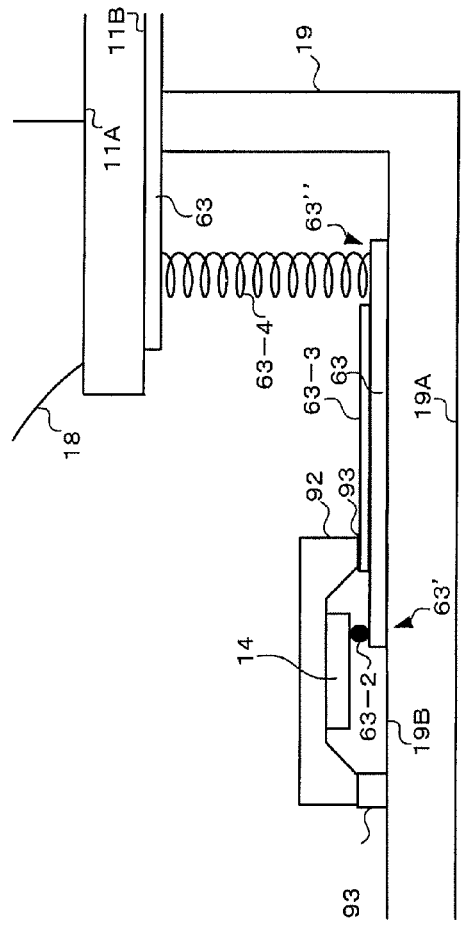
Fig. 13A
Fig. 13B

OPTICAL DEVICE AND BIOLOGICAL INFORMATION DETECTOR

CROSS-REFERENCE TO RELATED APPLICATIONS

This application claims priority to Japanese Patent Application No. 2010-071015 filed on Mar. 25, 2010. The entire disclosure of Japanese Patent Application No. 2010-071015 is hereby incorporated herein by reference.

BACKGROUND

1. Technical Field

The present invention relates to an optical device, a biological information detector, and similar devices.

2. Background Technology

A biological information measuring device measures human biological information such as, for example, pulse rate, blood oxygen saturation level, body temperature, or heart rate, and an example of a biological information measuring device is a pulse rate monitor for measuring the pulse rate. Also, a biological information measuring device such as a pulse rate monitor may be installed in a clock, a mobile phone, a pager, a PC, or another electrical device, or may be combined with the electrical device. The biological information measuring device has a biological information detector for detecting biological information, and the biological information detector includes a light-emitting element for emitting light towards a detection site of a test subject (i.e., a user), and a light-receiving element for receiving light having biological information from the detection site. Thus, a biological information detector or the biological information measuring device may have an optical device and be capable of detecting or measuring biological information. A common detector or a measuring device (or in a broader sense, an electronic device) other than a biological information detector or a biological information measuring device may also have an optical device.

In Patent Citation 1, there is disclosed a pulse rate monitor (or in a broader sense, a biological information measuring device). A light-receiving element (e.g., a light-receiving element 12 in FIG. 16 of Patent Citation 1) of the pulse rate monitor receives light reflected at a detection site (e.g., dotted line in FIG. 16 of Patent Citation 1) via a diffusion reflection plane (e.g., reflecting part 131 in FIG. 16 of Patent Citation 1). In an optical probe 1 in Patent Citation 1 (or in a broader sense, a biological information detector), a light-emitting element 11 and the light-receiving element 12 overlap with respect to a plan view, and the size of the optical probe 1 is reduced.

JP-A 2004-337605 (Patent Citation 1) is an example of the related art.

SUMMARY

Problems to Be Solved by the Invention

The light-emitting element 11 and the light-receiving element 12 in Patent Citation 1 are positioned, along with a substrate 15, in an interior of the reflecting part 131; and the interior of the reflecting part 131 is filled with a transparent material 142. The substrate 15 and a protecting part 16 (i.e., a contact part) must be disposed accurately with respect to each other so that a hole 161 on the protecting part 16 in FIG. 13 of Patent Citation 1 corresponds with the light-receiving element 12 on the substrate 15 in FIG. 3. Although a configuration of such description makes it possible to reduce the size of the optical probe 1, the optical probe 1 cannot be assembled with ease. Also, the protecting part 16 (i.e., the contact part) itself according to Patent Citation 1 inhibits transmission of light, and the detection accuracy of the biological information detector is poor.

According to several modes of the invention, it is possible to provide an optical device and a biological information detector that can be assembled with ease.

Means Used to Solve the Above-Mentioned Problems

A first aspect of the invention relates to an optical device, including a contact part having a contact surface and an opposing surface, the contact surface coming into contact with a test subject and the opposing surface being opposite the contact surface;

a support body installed on the opposing surface;

a first element supported by the support body; and a second element disposed between the opposing surface and the support body; wherein one of the first element and the second element is a light-emitting element for emitting light towards a detection site in the test subject;

another of the first element and the second element is a light-receiving element for receiving reflected light, the reflected light being light emitted by the light-emitting element and reflected at the detection site; and the contact part is formed from a material that is transparent with respect to a wavelength of the light emitted by the light-emitting element.

According to the first aspect of the invention, the contact part is formed from a material that is transparent with respect to the emission wavelength, and the contact part can therefore be disposed on a light path from the light-emitting element to the light-receiving element. Therefore, the support body for supporting the first element can be disposed on the opposing surface of the contact part. In an instance in which the first element is, e.g., the light-emitting element, the light emitted by the light-emitting element reaches the detection site of the test subject (e.g., a user) via the contact part. Specifically, there is no need to provide a hole on the contact part, and the support body can be readily disposed on the contact part. An optical device that can be readily assembled can thus be provided. Since the contact part is formed from a transparent material, light transmittance is increased, and the detection accuracy (i.e., signal-to-noise ratio) of the optical device is increased. Also, since the second element is disposed between the opposing surface and the support body, the size of the optical device can be reduced. Also, there is no need to separately provide a substrate between the first element and the second element, and the number of components is smaller. In an instance in which a substrate is provided on the light path between the light-emitting element and the light-receiving element, the substrate may inhibit transmission of light.

According to a second aspect of the invention, wiring for at least one of the first element and the second element may be formed on the opposing surface.

Thus, the opposing surface of the contact part can be made to function as a substrate. Specifically, there is no need to separately provide a substrate between the first element and the second element (i.e., a first substrate portion), nor is there a need to separately provide a substrate for establishing a connection to the exterior from at least one of the first element and the second element (i.e., a second substrate portion).

According to a third aspect of the invention, the optical device may further include
a reflecting part for reflecting the light emitted by the light-emitting element or the reflected light; and
a substrate, disposed between the support body and the reflecting part; wherein
the wiring may be electrically connected to a wiring formed on the substrate.

Thus, disposing the substrate (e.g., an external substrate including wiring for a control circuit (i.e., a third substrate portion)) between the support body and the reflecting part can make it easier to bring out the wiring to at least one of the first element and the second element.

According to a fourth aspect of the invention, the first element may be the light-receiving element, and the second element may be the light-emitting element.

Arranging the light-emitting element between the opposing surface and the support body thus makes it possible to reduce the distance between the light-emitting element and the detection site. Therefore, the amount of light reaching the detection site increases, and the detection accuracy of the optical device increases.

According to a fifth aspect of the invention, the support body may have an electroconductive support surface, and an electrode on a support surface-side of the light-receiving element may be electrically connected to the support surface.

In an instance in which the support surface is electroconductive, connecting, e.g., a bonding wire to the support surface thus makes it possible to readily extract a signal from the first element (i.e., the light-receiving element). Specifically, the first element (i.e., the light-receiving element) can be readily wired.

According to a sixth aspect of the invention, the light emitted by the light-emitting element may have a first light directed at the detection site and a second light directed in a direction other than that of the detection site, and the support body may have a reflecting surface for reflecting the second light towards the detection site.

Thus, the presence of the reflecting surface causes the second light, which does not directly reach the detection site of the test subject (e.g., the user), to reach the detection site via the reflecting surface. Therefore, the amount of light reaching the detection site increases, and the detection accuracy of the optical device increases. Also, the support body having the reflecting surface acts as the reflecting part, a dedicated reflecting part need not be separately provided, and the number of components is reduced.

According to a seventh aspect of the invention, the light-emitting element may be installed on the opposing surface.

Thus, the light-emitting element is attached to the opposing surface of the contact part using, e.g., a bump or another connecting member. Specifically, the distance between the light-emitting element and the detection site of the test subject (e.g., the user) can be reduced. Therefore, the amount of light reaching the detection site increases, and the detection accuracy of the optical device increases.

An eighth aspect of the invention relates to a biological information detector including the optical device described above, wherein the reflected light has pulse rate information.

According to the eighth aspect of the invention, an optical device that can be readily assembled can be used to readily assemble the entirety of the biological information detector (i.e., a pulse rate monitor).

BRIEF DESCRIPTION OF THE DRAWINGS

FIGS. 13A and 13B are schematic diagrams used to illustrate wiring for the light-emitting element;

DETAILED DESCRIPTION OF EXEMPLARY EMBODIMENTS

A description shall now be given for the present embodiment. The present embodiment described below is not intended to unduly limit the scope of the claims of the present embodiment. Not every configuration described in the present embodiment is necessarily an indispensible constituent feature of the invention.

1. Optical Device 1.1 First Example of Configuration

Figure 1A:
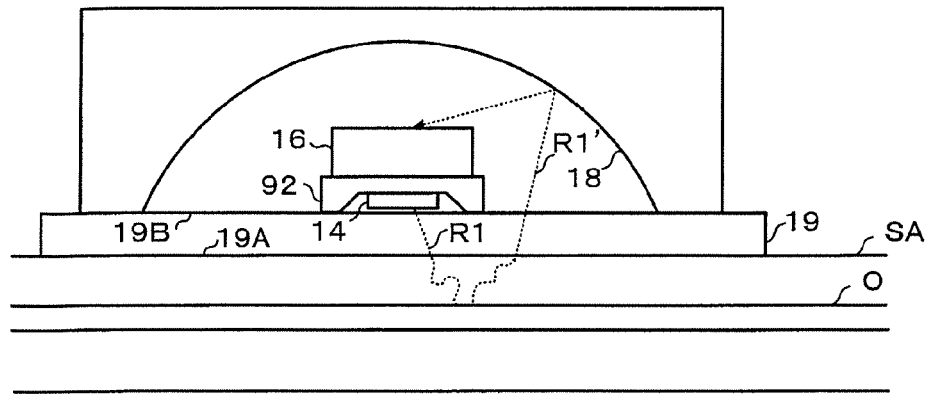
FIGS. 1A and 1B are examples of a configuration of an optical device according to a present embodiment.
Figure 1B:
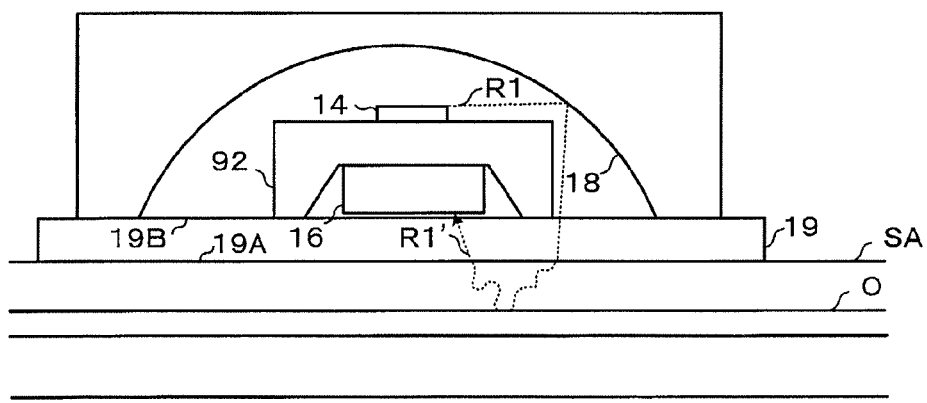

FIGS. 1A and 1B are examples of a configuration of an optical device according to a present embodiment. In FIGS. 1A and 1B, dimensions of each member are not intended to accurately represent actual dimensions. Specifically, in FIGS. 1A and 1B, dimensions of each of the members have been expanded or reduced in order to facilitate understanding of the descriptions given below. Similarly, drawings other than FIGS. 1A and 1B are not intended to necessarily represent actual dimensions.

As shown in FIGS. 1A and 1B, the optical device comprises a light-emitting element 14, a light-receiving element 16, a contact part 19, and a support body 92. The light-emitting element 14 emits light R1 directed at a detection site O in a test subject (e.g., a user). The light-receiving element 16 receives reflected light R1', which is light R1 emitted by the light-emitting element 14 and reflected at the detection site O. The contact part 19 has a contact surface 19A and an opposing surface 19B, the contact surface 19A coming into contact with the test subject and the opposing surface 19B being disposed opposite the contact surface 19A. The contact part 19 is formed from a material that is transparent with respect to the wavelength of the light R1 emitted by the light-emitting element 14 (e.g., glass). As shown in FIG. 1A, the contact part 19 can protect the light-emitting element 14, and as shown in FIG. 1B, the contact part 19 can protect the light-receiving element 16.

The support body 92 is installed on the opposing surface 19B and is made to support the first element. In the example shown in FIG. 1A, the light-receiving element 16, as the first element, is supported by the support body 92. In the example shown in FIG. 1B, the light-emitting element 14, as the first element, is supported by the support body 92. The second element is disposed between the opposing surface 19B and the support body 92, and the size of the optical device can therefore be reduced. In the example shown in FIG. 1A, the second element is the light-emitting element 14, and in the example shown in FIG. 1B, the second element is the light-receiving element 16. Thus, one of the first element and the second element is the light-emitting element 14 for emitting the light R1 directed at the detection site O of the test subject, and another of the first element and the second element is the light-receiving element 16 for receiving reflected light R1', which is light R1 emitted by the light-emitting element 14 and reflected at the detection site O.

The contact part 19 corresponds to, e.g., the protecting part 16 in Patent Citation 1. The protecting part 16 (i.e., the contact part) in Patent Citation 1 is not formed from a material that is transparent with respect to a wavelength of light emitted by the light-emitting element 11 in Patent Citation 1. Therefore, in the example shown in Patent Citation 1, the protecting part 16 (i.e., the contact part) is provided with a hole 161. Thus, in the example shown in Patent Citation 1, the light-emitting element 11 (or the light-receiving element 12) cannot be installed on the protecting part 16 (i.e., contact part), and the substrate 15 (i.e., a support part) for supporting the light-emitting element 11 (or the light-receiving element 12) is installed in the hole 161. The hole 161 and the light-emitting element 11 must be disposed accurately with respect to each other so that light passes through the hole 161. Therefore, the substrate 15 and the protecting part 16 must also be disposed accurately with respect to each other.

In the examples shown in FIGS. 1A and 1B, there is no need to necessarily provide a hole in the contact part 19. In an instance in which the contact part 19 is not provided with a hole, even in an instance in which the accuracy of positioning the support body 92 is poor, the light R1 emitted by the light-emitting element 14 reaches the detection site O of the test subject via the contact part 19. Specifically, the support body 92 can be readily disposed on the contact part 19. Thus, an optical device that can be readily assembled can be provided.

As shown in FIG. 13 in Patent Citation 1, in cross-section view, the protecting part 16 (i.e., the contact part) extends in an outward direction from a center of a circle that defines an inner surface (i.e., the reflecting part 131) of a main body 13. Taking FIG. 3 in Patent Citation 1 into account, the protecting part 16 (i.e., the contact part) itself inhibits transmission of light. Therefore, the amount of light reaching the light-emitting element 12 in Patent Citation 1 decreases, and the detection accuracy (i.e., the signal-to-noise ratio) of the biological information detector (or in a broader sense, the optical device) is poor.

In the example shown in FIGS. 1A and 1B, there is no need for the support body 92 to extend as with the protecting part 16 (i.e., the contact part) in FIG. 13 of Patent Citation 1, and the contact part 19 is formed from a transparent material. Therefore, light transmittance increases, and the detection accuracy (i.e., the signal-to-noise ratio) of the optical device increases.

As shown in FIGS. 1A and 1B, the optical device may further comprise a reflecting part 18. The optical device may also be modified so that the optical device has a structure that does not comprise the reflecting part 18 such as that shown in FIGS. 1A and 1B. In the example shown in FIG. 1A, the reflecting part 18 reflects the reflected light R1', and in the example shown in FIG. 1B, the reflecting part 18 reflects the light R1 emitted by the light-emitting element 14. The reflecting part 18 may have a reflecting surface on a dome surface (i.e., a spherical surface or a paraboloid) provided between the light-emitting element 14 and the light-receiving element 16.

In the example shown in FIGS. 1A and 1B, the detection site O (e.g., a blood vessel) is within the test subject. The first light R1 travels into the test subject and diffuses or scatters at the epidermis, the dermis, and the subcutaneous tissue. The first light R1 then reaches the detection site O, and is reflected at the detection site O. The reflected light R1' reflected at the detection site O diffuses or scatters at the subcutaneous tissue, the dermis, and the epidermis. The first light R1 is partially absorbed at the blood vessel. Therefore, due to an effect of a pulse, the rate of absorption at the blood vessel varies, and the amount of the reflected light R1' reflected at the detection site O also varies. Biological information (e.g. pulse rate) is thus reflected in the reflected light R1' reflected at the detection site O.

In an instance in which the reflected light R1' has pulse rate information (or in a broader sense, biological information), the optical device may be called a biological information detector. In the optical device (or in a narrower sense, the biological information detector), the light-emitting element 14 emits the light R1 directed at the detection site O of the test subject (e.g., the user). The light-receiving element 16 receives light R1' (i.e., the reflected light) having biological information, the light R1' being light R1 emitted by the light-emitting element 14 and reflected at the detection site O.

Examples of configurations of the optical device (or in a narrower sense, the biological information detector) are not limited by those shown in FIGS. 1A and 1B, and the shape, or a similar attribute, of a part of the example of configuration (e.g., the light-receiving element 16) may be modified. The biological information may also be blood oxygen saturation level, body temperature, heart rate, or a similar variable; and the detection site O may be positioned at a surface SA of the test subject. In the examples shown in FIGS. 1A and 1B, the first light R1 is shown by a single line; however, in reality, the light-emitting element 14 emits many light beams in a variety of directions.

1.2 First Comparative Example

Figure 2A:
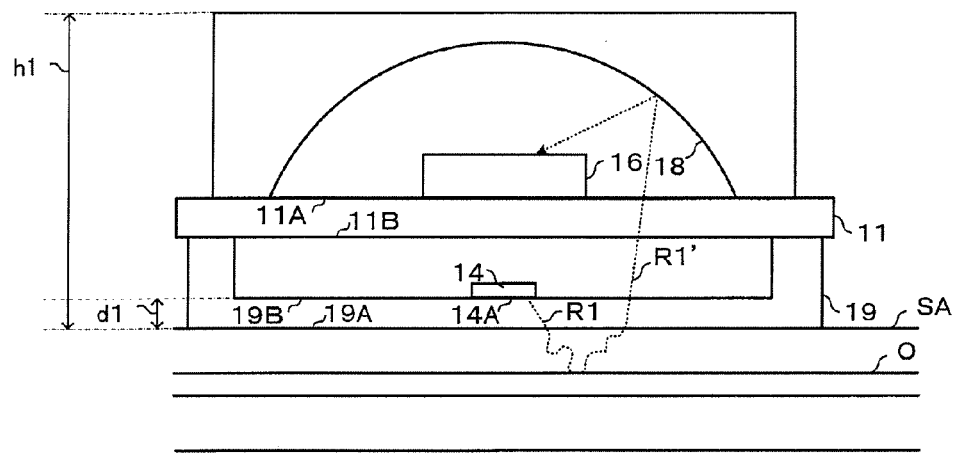
FIGS. 2A and 2B are examples used for purposes of comparison to the examples shown in FIG. 1.
Figure 2B:
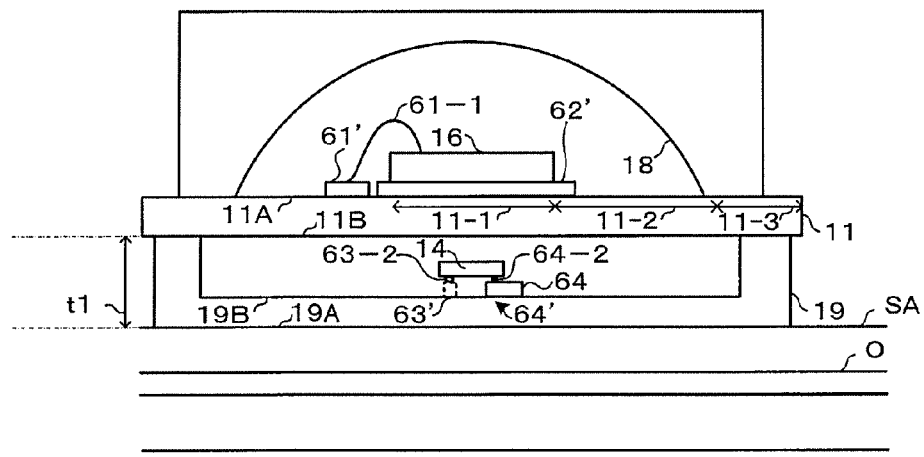

FIGS. 2A and 2B are an example used for purposes of comparison to the configuration examples shown in FIG. 1 (or the configuration example shown in Patent Citation 1). Structures that are identical to those in the examples described above are identified with the same numerals, and a description of the structures is not provided. The example shown in FIGS. 2A and 2B is a comparative example but has a novel configuration. In the example shown in FIGS. 2A and 2B, the light-emitting element 14 is disposed on a side towards the detection site O as shown in FIG. 1A.

In the example shown in FIGS. 2A and 2B, the shape of the contact part 19 is modified so that the contact part 19 in FIG. 1 has a depression. Also, in the example shown in FIGS. 2A and 2B, the optical device (or in a broader sense, the biological information detector) may further comprise a substrate 11. Alternatively, the substrate 11 may be provided so as to be disposed instead of the support body 92. The substrate 11 has a first surface 11A and a second surface 11B that is opposite the first surface 11A, and is formed from a material that is transparent with respect to the wavelength of the light R1 emitted by the light-emitting element 14 (e.g., polyimide). The substrate 11 may support, e.g., the light-receiving element 16, as shown, e.g., in FIG. 2A. The example shown in FIGS. 2A and 2B has the following advantages over the example in Patent Citation 1.

Since the substrate 11 is disposed between the reflecting part 18 and the contact part 19, even in an instance in which the light-receiving element 16 is disposed on the substrate 11, there is no need to separately provide a mechanism for supporting the substrate 11 itself, and the number of components is reduced. Also, since the substrate 11 is formed from a material that is transparent with respect to the emission wavelength, the substrate 11 can be disposed on a light path from the light-emitting element 14 to the light-receiving element 16, and there is no need to accommodate the substrate 11 at a position away from the light path, such as within the reflecting part 18. An optical device (or in a broader sense, a biological information detector) that can be readily assembled can thus be provided.

In Patent Citation 1, it is necessary to install the light-emitting element 11, the light-receiving part 12, the substrate 15, and the transparent material 142 in the interior of the reflecting part 131. Therefore, a small optical probe 1 cannot be assembled with ease. Also, according to paragraph [0048] in Patent Citation 1, the substrate 15 is formed so that an interior-side of the reflecting part 131 is a diffuse reflection surface. In other words, the substrate 15 in Patent Citation 1 is not required to be formed from a transparent material.

However, as shown in FIG. 2A, the reflected light R1' passes through not only the contact part 19 but also the substrate 11. In other words, the amount of reflected light R1' is attenuated not only in the contact part 19, but also in the substrate 11. Therefore, in the example shown in FIGS. 2A and 2B, the detection accuracy of the optical device is poor, compared to the examples shown in FIG. 1. Also, the presence of the depression (i.e., t1−d1) and other structures increases the height (h1) of the optical device. t1 represents the thickness of the contact part 19 such as that shown in FIG. 2B, and d1 represents the distance between a first light-emitting surface 14A of the light-emitting element 14 and the surface SA of the test subject such as those shown in FIG. 2A.

The example shown in FIGS. 2A and 2B has a configuration that results in other advantages as described below. A specific description is given as follows; the configuration can also be applied to the examples shown in FIG. 1.

As shown in FIG. 2A, the light-emitting element 14 is installed on the opposing surface 19B. Wiring for the light-emitting element 14 and wiring for the light-receiving element 16 are not shown in the example shown in FIG. 2A, but can be represented as shown, e.g., in FIG. 2B. The example shown in FIG. 2B shows a cross-section view along a cut plane. In reality, wiring other than that shown in the example of FIG. 2B is also present. In the example shown in FIG. 2B, a connection pad 63' and a bump 63-2 that are not, in reality, present in the cut plane, are represented by a dotted line and a white circle. In the example shown in FIG. 2B, a part of a wiring 64 for the light-emitting element 14 is shown. The wiring 64 has a pad 64' for providing a connection with the light-emitting element 14. The pad 64' for providing a connection with the light-emitting element 14 (or in a broader sense, a first wiring for the light-emitting element 14) is disposed on the opposing surface 19B, and the light-emitting element 14 is installed on a surface of the pad 64' for providing a connection with the light-emitting element 14. In the example shown in FIG. 2B, the light-emitting element 14 is, e.g., mounted on the surface of the connection pad 64' (or in a broader sense, the opposing surface 19B of the contact part 19) using, e.g., a bump 64-2 or another connecting member.

Since the light-emitting element 14 is installed on the opposing surface 19B, the distance between the light-emitting element 14 and the detection site O of the test subject (e.g., the user) can be reduced. Therefore, the amount of light reaching the detection site O increases, and the detection accuracy (i.e., signal-to-noise ratio) of the biological information detector increases. Meanwhile, according to Patent Citation 1, the light-emitting element 11 and the light-receiving element 12 are disposed, with the substrate 15, in the interior of the reflecting element 131; and the interior of the reflecting element 131 is filled with the transparent material 142. According to a configuration of such description, a predetermined distance is present between the light-emitting element 11 and the detection site, and the detection accuracy of the biological information detector is poor.

In the example shown in FIG. 2B, the connection pad 64' is connected, e.g., to an anode of the light-emitting element 14 via the bump 64-2 (e.g., a gold bump, a solder bump etc.). In the example shown in FIG. 2B, the connection pad 63' shown by a dotted line is connected, e.g., to a cathode of the light-emitting element 14 via the bump 63-2 shown by a white circle. In the example shown in FIG. 2B, a part of a wiring for the light-receiving element 16 is shown, and a pad 61' for providing a connection to the light-receiving element 16 is shown. The connection pad 61' is connected, e.g., to an anode of the light-receiving element 16 via a bonding wire 61-1. In the example shown in FIG. 2B, a connecting part 62' in contact with, e.g., a cathode of the light-receiving element 16 is also shown as a part of a wiring for the light-receiving element 16. The connecting part 62' is directly connected to the cathode of the light-receiving element 16 via, e.g., an adhesive (not shown). A silver paste, for example, can be used as an electroconductive adhesive (or in a broader sense, a connecting member).

The thickness of the substrate 11 is e.g., 10 μm to 1000 μm. Wiring for the light-emitting element 14 and wiring for the light-receiving element 16 may be formed on the substrate 11. The substrate 11 is, e.g., a printed circuit board; however, a printed circuit board is not generally formed from a transparent material, as with the substrate 15 of Patent Citation 1. Specifically, the inventors purposefully used a configuration in which the printed circuit board is formed from a material that is transparent at least with respect to the emission wavelength of the light-emitting element 14. The thickness of the protecting part 19 is, e.g., 1 μm to 3000 μm.

The light-emitting element 14 is, for example, an LED. The light emitted by the LED has a maximum intensity (or in a broader sense, a peak intensity) within a wavelength range of, e.g., 425 nm to 625 nm, and is, e.g., green in color. The thickness of the light-emitting element 14 is, e.g., 20 μm to 1000 μm. The light-receiving element 16 is, e.g., a photodiode, and can generally be formed by a silicon photodiode. The thickness of the light-receiving element 16 is, e.g., 20 μm to 1000 μm. The silicon photodiode has a maximum sensitivity (or in a broader sense, a peak sensitivity) for received light having a wavelength within a range of, e.g., 800 nm to 1000 nm. Preferably, the light-receiving element 16 is formed by a gallium arsenide phosphide photodiode, and the gallium arsenide phosphide photodiode has a maximum sensitivity (or in a broader sense, a peak sensitivity) for received light having a wavelength within a range of, e.g., 550 nm to 650 nm. Since biological substances (water or hemoglobin) readily allow transmission of infrared light within a range of 700 nm to 1100 nm, the light-receiving element 16 formed by the gallium arsenide phosphide photodiode is more capable of reducing noise components arising from external light than the light-receiving element 16 formed by the silicon photodiode.

Figure 3A:
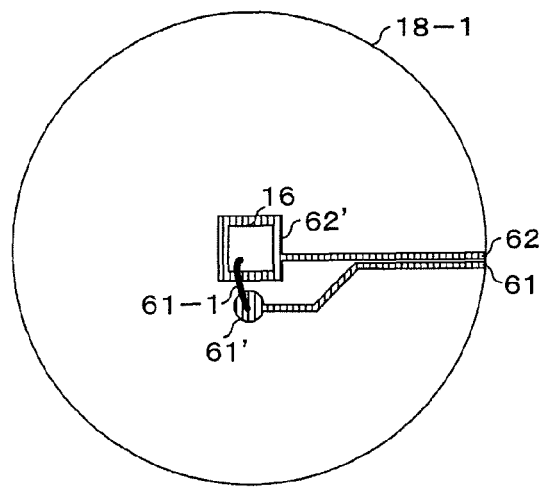
FIGS. 3A, 3B, and 3C are plan views of the optical device shown in FIG. 2B.
Figure 3B:
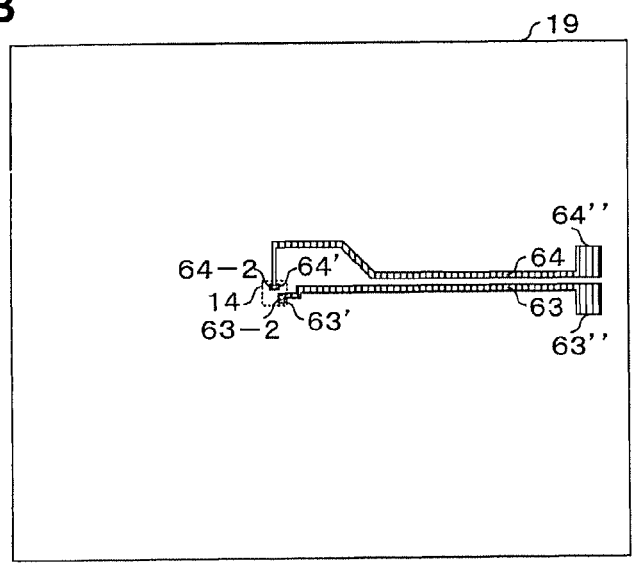
Figure 3C:
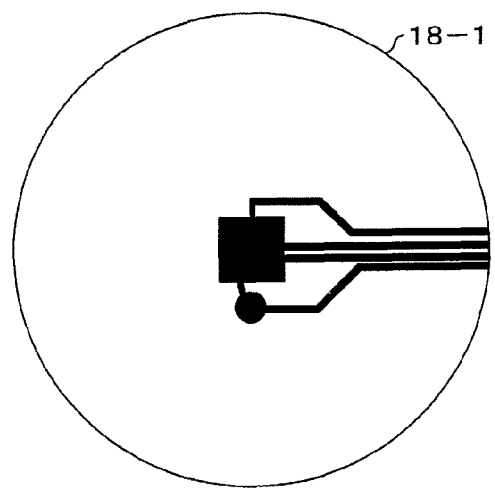

FIGS. 3A, 3B, and 3C are plan views of the optical device shown in FIG. 2B. FIG. 3A corresponds to a plan view of a side towards the light-receiving element 16, FIG. 3B corresponds to a plan view of a side towards the light-emitting element 14, and FIG. 3C corresponds to a light-blocking region including the light-receiving element 16 and the light-emitting element 14. FIGS. 3A and 3C show only a region of irradiation in which the light R1' having biological information (i.e., the reflected light) travels to the substrate 11. The irradiation region may be defined, e.g., by a boundary 18-1 between the reflecting surface of the reflecting element 18 (i.e., the dome surface in the example shown in FIGS. 2A and 2B) and the substrate 11. The boundary 18-1 has, for example, a circular profile.

As shown in FIG. 3A, with respect to a plan view (e.g., when viewed from the side of the light-receiving element 16 in FIG. 2B), a wiring 61 that connects to the anode (or in a broader sense, an electrode) of the light-receiving element 16 is formed on the substrate 11. A wiring 62 that connects to the cathode (or in a broader sense, an electrode) of the light-receiving element 16 is also formed on the substrate 11. In the example shown in FIG. 3A, the wiring 61 has the pad 61' for providing a connection with the light-receiving element 16, and the bonding wire 61-1. The connection pad 61' of the wiring 61 is connected to the anode of the light-receiving element 16 via the bonding wire 61-1. In the example shown in FIG. 3A, the wiring 62 has the connecting part 62' in contact with the cathode of the light-receiving element 16.

As shown in FIG. 3B, with respect to a plan view (e.g., when viewed from the side of the light-emitting element 14 in FIG. 2B), a wiring 63 for providing a connection with the cathode of the light-emitting element 14 is formed on the contact part 19 (or in a narrower sense, the opposing surface 19B). The wiring 64 for providing a connection with the anode of the light-emitting element 14 is also formed on the contact part 19 (or in a narrower sense, the opposing surface 19B). In the example shown in FIG. 3B, the wiring 63 has a pad 63' for providing a connection with the light-emitting element 14, and the bump 63-2. The connection pad 63' of the wiring 63 is connected to the cathode of the light-emitting element 14 via the bump 63-2. Also, the wiring 63 may comprise a connection pad 63". In the example shown in FIG. 3B, the wiring 64 has the pad 64' for providing a connection with the light-emitting element 14, and the bump 64-2. The connection pad 64' of the wiring 64 is connected to the anode of the light-emitting element 14 via the bump 64-2. Also, the wiring 64 may comprise a connection pad 64".

The configuration of the wiring 63 and the wiring 64 for the light-emitting element 14 and the wiring 61 and the wiring 62 for the light-receiving element 16 is not limited by the examples shown in FIGS. 3A and 2B. For example, the shape of the connection pad 61' of the wiring 61 may, instead of being circular as shown in FIG. 3A, be, e.g., square, elliptical, polygonal, or describing another shape. The shape of the connection pads 63', 63" of the wiring 63 may, instead of being square as shown in FIG. 3B, also be, e.g., circular, elliptical, polygonal, or describing another shape. Also, although in the example shown in FIG. 3A, the light-receiving element 16 has the cathode on a bottom surface, the light-receiving element 16 may have the cathode on a front surface in a similar manner to the anode.

As shown, for example, in FIG. 2A, in an instance in which the light R1' having the biological information (i.e., the reflected light) is directed to the substrate 11, the light R1' having the biological information (i.e., the reflected light) reaches the opposing surface 19B of the contact part 19. In an instance in which the wiring 63 and the wiring 64 for the light-emitting element 14 are present as shown in FIG. 3B, at least the wiring 63 and the wiring 64 block or reflect the light R1' having the biological information (i.e., the reflected light) and form a light-blocking region. Also, even in an instance where the light R1' having the biological information (i.e., the reflected light) enters an interior of the substrate 11, in an instance where the wiring 61 and the wiring 62 for the light-receiving element 16 are present as shown in FIG. 3A, at least the wiring 61 and the wiring 62 inhibit the light R1' having the biological information (i.e., the reflected light) from leaving the interior towards an exterior of the substrate 11. The light-blocking region of the contact part 19 and the substrate 11, where the wiring 61, the wiring 62, the wiring 63, and the wiring 64 are positioned thus inhibit the light R1' having the biological information (i.e., the reflected light) from reaching the reflecting part 18. Specifically, the light R1' having the biological information (i.e., the reflected light) is capable of passing through a region of the substrate 11 excluding the light-blocking region of the contact part 19 and the substrate 11.

FIG. 3C shows a light-blocking region within the irradiation region. The light-blocking region is shown in black in the example shown in FIG. 3C. As shown in FIG. 3C, the light-blocking region can be defined, with respect to the plan view, by the wiring 61 (including the connection pad 61' and the bonding wire 61-1) and the wiring 62 (including the connecting part 62') shown in FIG. 3A, and the wiring 63 (including the connection pad 63' and the bump 63-2) and the wiring 64 (including the connection pad 64' and the bump 64-2) shown in FIG. 3B.

1.3 Second Comparative Example

Figure 4A:
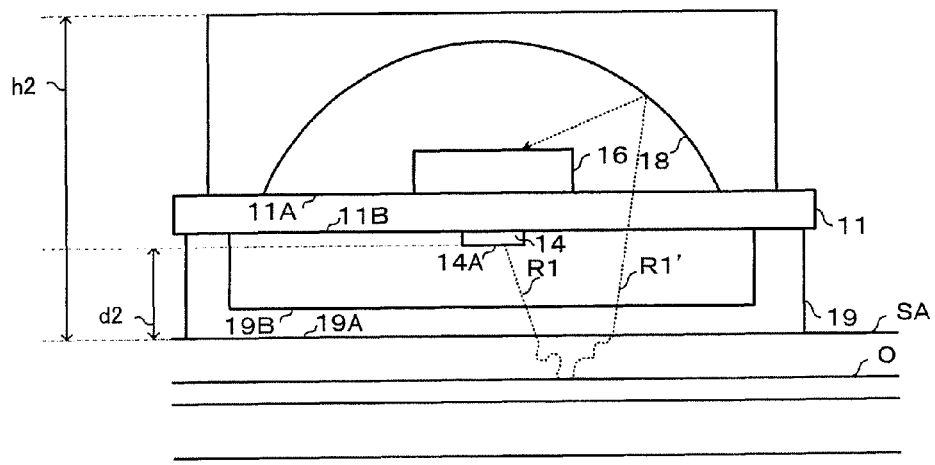
FIGS. 4A and 4B are other examples for purposes of comparisons to the examples shown in FIG. 1.
Figure 4B:
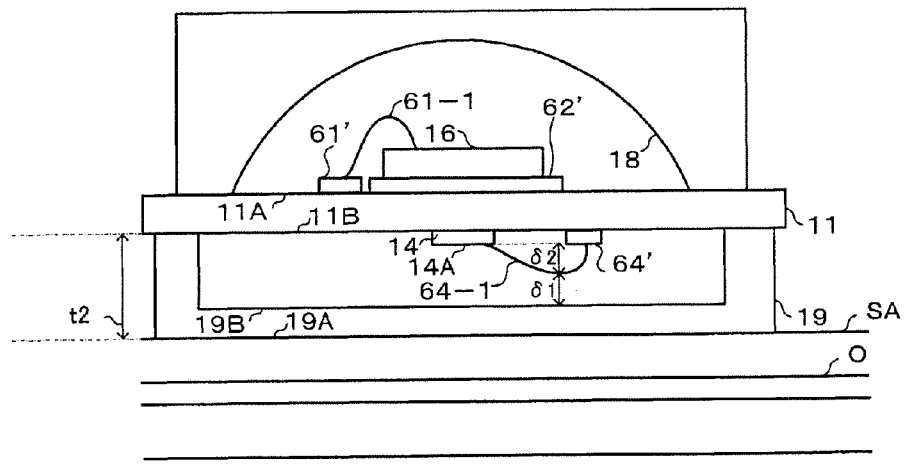

FIGS. 4A and 4B are another example used for purposes of comparison to the configuration examples shown in FIG. 1 (or the configuration example in Patent Citation 1). Structures that are identical to those in the examples described above are identified using the same numerals, and a description of the structures is not provided. The example shown in FIGS. 4A and 4B is a comparative example but has a novel configuration. In the example shown in FIG. 4A, the light-emitting element 14 is disposed on the second surface 11B of the substrate 11. Specifically, as shown in FIG. 4B, the pad 64' for providing a connection with the light-emitting element 14 (or in a broader sense, the first wiring for the light-emitting element 14) is disposed on the second surface 11B, and the connection pad 64' is connected to, e.g., the anode of the light-emitting element 14 via a bonding wire 64-1.

As shown in the example shown in FIG. 2, the light-emitting element 14 shown, e.g., in FIG. 1A is preferably installed on the opposing surface 19B. However, the light-emitting element 14 shown, e.g., in FIG. 1A may not be installed on the opposing surface 19B, as shown in the example in FIG. 4. Specifically, the light-emitting element 14 in FIG. 1A is preferably attached to the opposing surface 19B of the contact part 19 using, e.g., a bump or another connecting member. However, a bonding wire or a similar structure may be used instead of the bump. In an instance in which the light-emitting element 14 is installed on the opposing surface 19B, the detection accuracy of the optical device increases, and the size of the optical device can be reduced, as described further below.

In the example shown in FIG. 4A, the distance between a first light-emitting surface 14A that faces the detection site O and emits a first light R1, and the surface SA of the test subject, is represented by d2. In FIG. 2A, the distance between the first light-emitting surface 14A and the surface SA of the test subject is represented by d1. Since the light-emitting element 14 is installed on the opposing surface 19B in the example shown in FIG. 2A, d1 is smaller than d2. Since the distance between the light-emitting element 14 and the detection site O is therefore shorter, the amount of light reaching the detection site O increases, and the detection accuracy (i.e., the signal-to-noise ratio) of the biological information detector increases.

In an instance in which the light-emitting element 14 is disposed on the second surface 11B of the substrate 11 as shown in FIG. 4B, the bonding wire 64-1 becomes necessary. The bonding wire 64-1 is between the connection pad 64' and the anode of the light-emitting element 14. As shown in FIG. 4B, the bonding wire 64-1 describes an arc, and the height or the depth of the bonding wire 64-1 (i.e., the arc) is represented by $\delta 2$. $\delta 2$ is, e.g., 120 μm. A gap represented by $\delta 1$ in FIG. 4B is assigned so that the contact part 19 does not damage the bonding wire 64-1. $\delta 1$ is, e.g., 300 μm. When error during manufacture of the bonding wire 64-1 and flexure of the substrate 11 is taken into account, $\delta 1$ must not be zero.

Therefore, the thickness t2 of the contact part 19 shown in FIG. 4B is larger than the thickness t1 of the contact part 19 shown in FIG. 2B. The height h2 of the biological information detector shown in FIG. 4A is thereby larger than the height h1 of the biological information detector shown in FIG. 2A. Specifically, in the example shown in FIGS. 2A and 2B, the biological information detector can be made smaller.

Figure 5A:
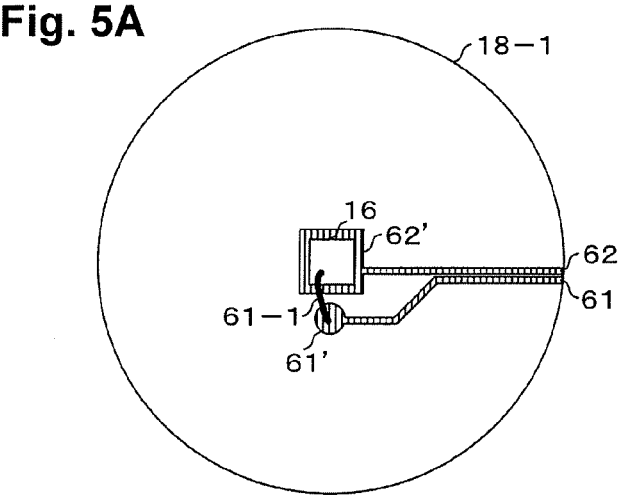
FIGS. 5A, 5B, and 5C are plan views of the optical device shown in FIG. 4B.
Figure 5B:
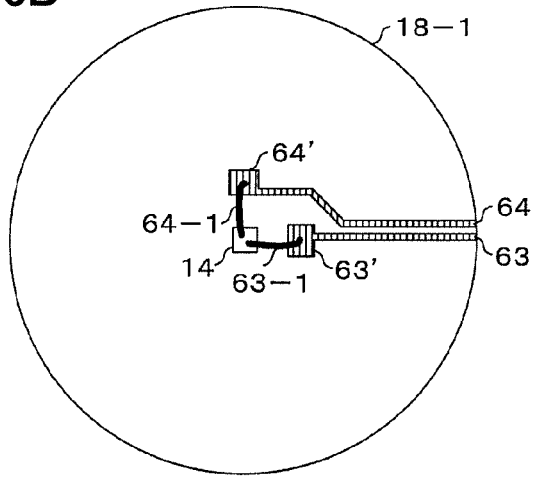
Figure 5C:
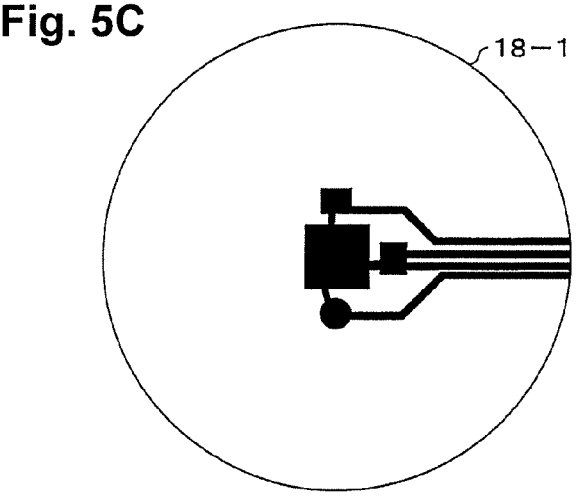

FIGS. 5A, 5B, and 5C are plan views of the biological information detector shown in FIG. 4B. FIG. 5A corresponds to a plan view of a side towards the light-receiving element 16, FIG. 5B corresponds to a plan view of a side towards the light-emitting element 14, and FIG. 5C corresponds to a light-blocking region including the light-receiving element 16 and the light-emitting element 14. Structures that are identical to those in the examples described above are identified with the same numerals, and a description of the structures is not provided. FIG. 5A matches FIG. 3A. However, in the example of FIG. 5B, the wiring 63 has a pad 63' for providing a connection with the substrate 41, and a bonding wire 63-1. The connection pad 63' of the wiring 63 is connected to the cathode of the light-emitting element 14 via the bonding wire 63-1. In the example of FIG. 5B, the wiring 64 has the pad 64' for providing a connection with the light-emitting element 14, and the bonding wire 64-1. The connection pad 64' of the wiring 64 is connected to the anode of the light-emitting element 14 via the bonding wire 64-1.

The connection pad 63' and the connection pad 64' of FIG. 5B are respectively connected to the bonding wire 63-1 and the bonding wire 64-1, the connection being established externally with respect to the light-emitting element 14. Therefore, the light-blocking region shown in FIG. 3C is smaller than the light-blocking region shown in FIG. 5C. Accordingly, in the example shown in FIG. 3C, the light R1' having biological information (i.e., the reflected light) can readily reach the light-receiving element 16, and the detection accuracy (i.e., the signal-to-noise ratio) of the biological information detector increases.

1.4 Second Configuration Example

Figure 6A:
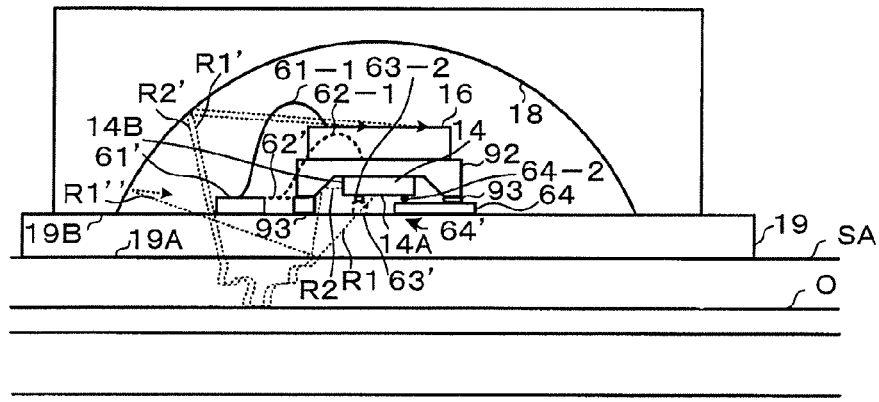
FIGS. 6A and 6B are other examples of a configuration of the optical device according to the present embodiment.
Figure 6B:
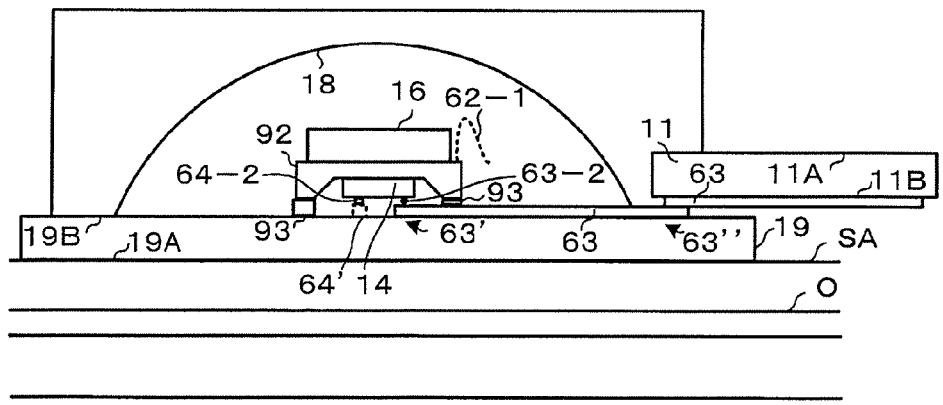

FIGS. 6A and 6B show another example of configuration of the optical device according to the present embodiment. A cross-section view shown in FIG. 6A corresponds to the cross-section view shown in FIG. 1A, and FIG. 6B is a cross-section view corresponding to a cut surface that is different from a cut surface shown in FIG. 6A. Structures that are identical to those in the examples described above are identified with the same numerals, and a description of the structures is not provided. As shown in FIGS. 6A and 6B, the support body 92 also functions as a reflecting part. In an instance in which the support body 92 is referred to as a first reflecting part, the reflecting part 18 may be referred to as a second reflecting part. In the example shown in FIGS. 6A and 6B, the support body 92 (i.e., the first reflecting part) is secured to the opposing surface 19B of the contact part 19. The support body 92 can be secured using, e.g., an adhesive 93.

As shown in FIG. 6A, the light-emitting element 14 emits a first light R1 directed at the detection site O of the test subject (e.g., the user) and a second light R2 directed in a direction other than that of the detection site O (i.e., directed at the reflecting surface of the support body 92). The support body 92 (i.e., the first reflecting part) causes the second light R2 to be reflected and guided towards the detection site O. The light-receiving element 16 receives lights R1' and R2' having biological information (i.e., reflected light; valid light), which are, respectively, the first light R1 and the second light R2 reflected at the detection site O. The second reflecting part 18 causes the lights R1' and R2' having biological information (i.e., reflected light) from the detection site O to be reflected and guided towards the light-receiving element 16. Due to the presence of the support body 92 (i.e., the first reflecting part), the second light R2, which does not directly reach the detection site O of the test subject (i.e., the user), also reaches the detection site O. Specifically, the amount of light reaching the detection site O via the support body 92 (i.e., the first reflecting part) increases, and the efficiency of the light-emitting element 14 increases. Therefore, the detection accuracy (i.e., the signal-to-noise ratio) of the optical device (or in a narrower sense, the biological information detector) increases. The support body 92 thus has a reflecting surface for reflecting the second light R2 towards the detection site O.

In Patent Citation 1, there is disclosed a structure corresponding to the second reflecting part 18 (i.e., the reflecting part 131 in FIG. 16 of Patent Citation 1). Specifically, the light-receiving element 12 in FIG. 16 of Patent Citation 1 receives light reflected at the detection site via the reflecting part 131. However, in Patent Citation 1 a structure corresponding to the support body 92 is not disclosed. In other words, at the time of application, those skilled in the art have not identified an issue of increasing the efficiency of the light-emitting element 11 in FIG. 16 in Patent Citation 1.

In the example shown in FIG. 6A, the light-emitting element 14 is installed on the opposing surface 19B of the contact part 19 as shown in FIG. 2B. The wiring 64 for the light-emitting element 14 is formed on the opposing surface 19B. In the example shown in FIG. 6B, the wiring 63 for the light-emitting element 14 is also formed on the opposing surface 19B. Wirings 61, 62, not shown in FIGS. 6A and 6B, for the light-receiving element 16 can be formed on the opposing surface 19B (see FIG. 7A).

Since wirings 61, 62, 63, 64 for at least one of the light-emitting element 14 and the light-receiving element 16 are formed on the opposing surface 19B of the contact part 19, the opposing surface 19B of the contact part 19 can be made to function as a substrate. Specifically, there is no need to separately provide a substrate between the light-emitting element 14 and the light-receiving element 16 (e.g., a first substrate portion 11-1 shown in FIG. 2B), nor is there a need to separately provide a substrate for establishing a connection to the exterior from at least one of the light-emitting element 14 and the light-receiving element 16 (e.g., a second substrate portion 11-2 shown in FIG. 2B).

As shown in FIG. 6B, which shows a cross-section view corresponding to a cut surface that is different from the cut surface shown in FIG. 6A, the optical device may comprise a substrate 11 disposed between the contact part 19 and the reflecting part 18. In the example shown in FIG. 6B, the wiring 63 for the light-emitting element 14 formed on the opposing surface 19B is electrically connected to wiring 63 formed on the substrate 11. Additionally, the wiring 64 for the light-emitting element 14 and the wirings 61, 62 for the light-receiving element 16, not shown in FIG. 6B, can also be respectively electrically connected to wirings 64, 61, and 62 formed on the substrate 11 (see FIGS. 7A, 7B, and 7C).

Thus, disposing the substrate 11 (e.g., a third substrate portion 11-3 shown in FIG. 2B) between the support body 19 and the reflecting part 18 can make it easier to bring out the wirings 61, 62, 63, and 64 to at least one of the light-emitting element 14 and the light-receiving element 16. In contrast to the example shown in FIG. 6B, a hole (not shown) may be formed on, e.g., the reflecting part 18, and the wirings 61, 62, 63, 64 may be passed through the hole. Also, in an instance in which the wirings 61, 62, 63, and 64 for at least one of the light-emitting element 14 and the light-receiving element 16 formed on the substrate 11 in FIG. 6B are wirings for a control circuit for controlling at least one of the light-emitting element 14 or the light-receiving element 16 formed on, e.g., a motherboard (not shown), the substrate 11 may be referred to as an external substrate.

The substrate 11 has a first surface 11A (e.g., a front surface) and a second surface 11B (e.g., a reverse surface) that is opposite the first surface 11A. The substrate 11, such as that shown in FIG. 6B, may have wirings 61, 62, 63, 64 formed only on the second surface 11B. In an instance in which the light-emitting element 14 and the light-receiving element 16 are disposed above and below the substrate 11 as shown, e.g., in FIGS. 2B and 4B, the substrate 11 of such description is provided with the wirings 61, 62 formed on the first surface 11A and the wirings 63, 64 formed on the second surface 11B. In an instance in which the wirings 61, 62, 63, 64 are formed on both surfaces of the substrate 11, the manufacturing cost is increased. Specifically, in the example shown in FIG. 6B, the wirings 61, 62, 63, 64 are formed on one surface of the substrate 11, and the manufacturing cost can be reduced. Also, in the example shown in FIG. 6B, the substrate 11 is not required to comprise a light-transmitting part that causes the amount of light to attenuate (e.g., the second substrate portion 11-2 shown in FIG. 2B). Therefore, the light transmittance increases, and the detection accuracy (i.e., the signal-to-noise ratio) of the optical device increases.

In the example shown in FIG. 6A, a bonding wire 62-1 is also present in addition to the bonding wire 61-1. In the example shown in FIG. 6A, the bonding wire 62-1 is shown by a dotted line. In the example shown in FIG. 2B, the connecting part 62' is directly connected to the cathode of the light-receiving element 16. In the example shown in FIG. 6A, the connecting part 62' shown by a dotted line can be formed as a connection pad (see FIG. 7A). In the example shown in FIGS. 6A and 6B, the bonding wire 62-1 electrically connects the connecting part 62' (i.e., the connection pad) to a support surface of the support body 92 (see support surface 92-5 in FIGS. 10A, 10B, and 10C). In the example shown in FIGS. 6A and 6B, the support surface of the support body 92 supports the light-receiving element 16 (or in a broader sense, the first element) and is electroconductive. A reverse-surface electrode of the light-receiving element 16 (or in a narrower sense, a cathode; an electrode of the light-receiving element 16 that is disposed on a surface towards the support surface) is electrically connected to the support surface. The support surface of the support body 92 is directly connected to the reverse-surface electrode (or in a narrower sense, the cathode) of the light-receiving element 16 with, e.g., an adhesive (not shown) interposed therebetween. A silver paste, for example, can be used as an electroconductive adhesive (or in a broader sense, a connecting member).

In FIG. 6B, a part of the bonding wire 62-1 is not shown. However, the bonding wire 62-1 is actually connected to the connecting part 62' (i.e., connection pad), as shown in FIG. 6A. Also, in FIG. 6B, the dimensions of the substrate 11 are not intended to be necessarily accurate. Specifically, in an instance in which the substrate 11 is disposed between the contact part 19 and the reflecting part 18, the reflecting part 18 does not necessarily need to be machined for the substrate 11 to be inserted.

Figure 7A:
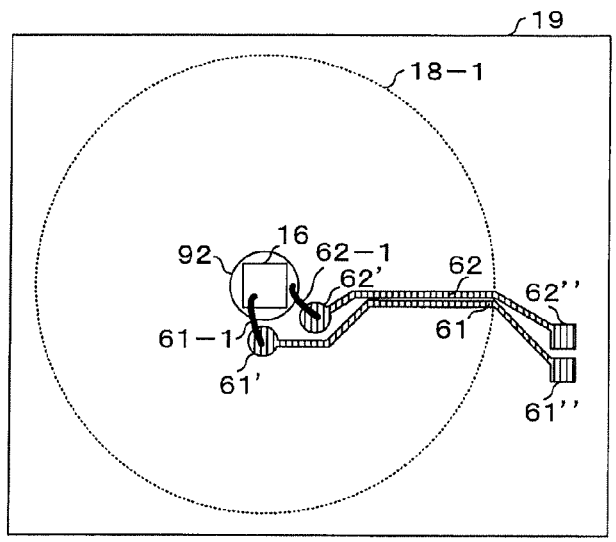
FIGS. 7A, 7B, and 7C are plan views of the optical device shown in FIGS. 6A and 6B.
Figure 7B:
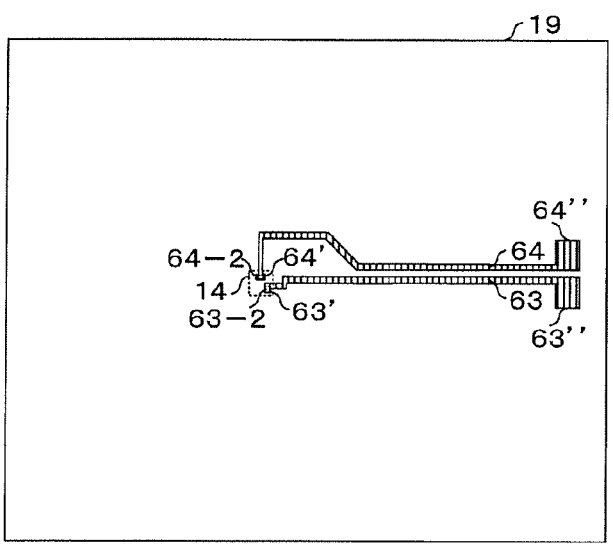
Figure 7C:
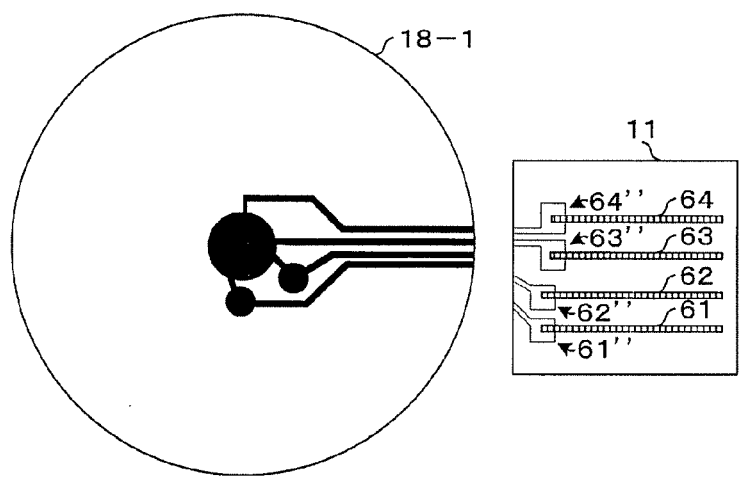

FIGS. 7A, 7B, and 7C are plan views of the optical device shown in FIGS. 6A and 6B. FIG. 7A corresponds to a plan view showing mainly the light-receiving element 16 and the support body 92 (i.e., the first reflecting part), FIG. 7B corresponds to a plan view showing mainly the light-emitting element 14, and FIG. 7C corresponds not only to a light-blocking region that includes the light-receiving element 16 and the light-emitting element 14, but also to the substrate 11. Structures that are identical to those in the examples described above are identified with the same numerals, and a description of the structures is not provided.

In the example shown in FIGS. 6A and 6B, the light-receiving element 16 is disposed on the support body 92 rather than the substrate 11. Therefore, FIG. 7A shows the light-receiving element 16 that is disposed on the contact part 19 with the support body 92 interposed therebetween. In FIG. 7A, the boundary 18-1 between the domed surface of the reflecting part 18 and the contact part 19 is shown by a dotted line. In the example shown in FIG. 7A, the wiring 61 includes a connection pad 61", and the wiring 62 includes a connection pad 62".

FIG. 7C shows the substrate 11, and each of the connection pads 61", 62", 63", 64" is shown by a fine line. The wirings 61, 62, 63, 64 formed on the contact part 19 are respectively electrically connected to wirings 61, 62, 63, 64 formed on the substrate 11 via connection pads 61", 62", 63", 64" interposed therebetween (see FIGS. 6B, 7A, 7B, and 7C).

Figure 8:
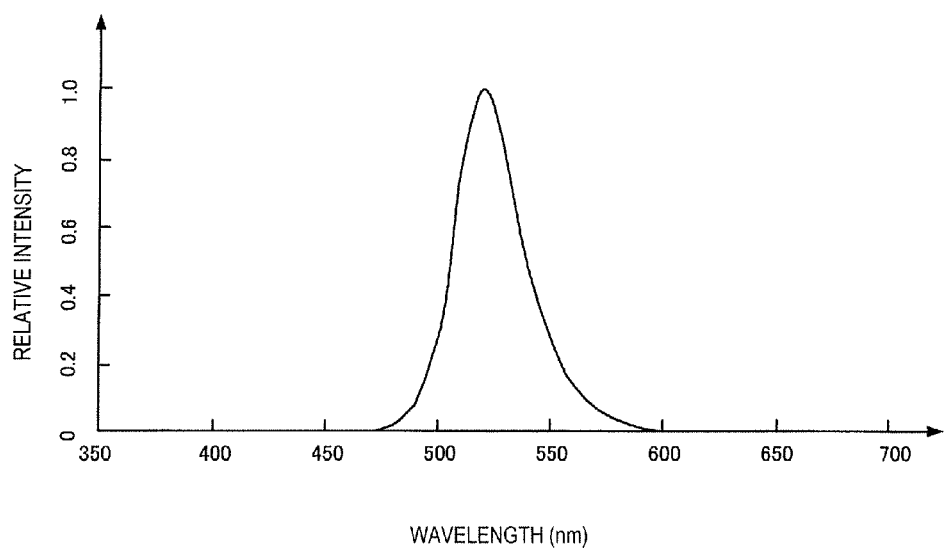
FIG. 8 is an example of intensity characteristics of light emitted by the light-emitting element.

FIG. 8 shows an example of intensity characteristics of the light emitted by the light-emitting element 14. In the example shown in FIG. 8, the intensity is at a maximum for light having a wavelength of 520 nm, and the intensity of light having other wavelengths is normalized with respect thereto. Also, in the example shown in FIG. 8, the wavelengths of light emitted by the light-emitting element 14 are within a range of 470 nm to 600 nm.

Figure 9:
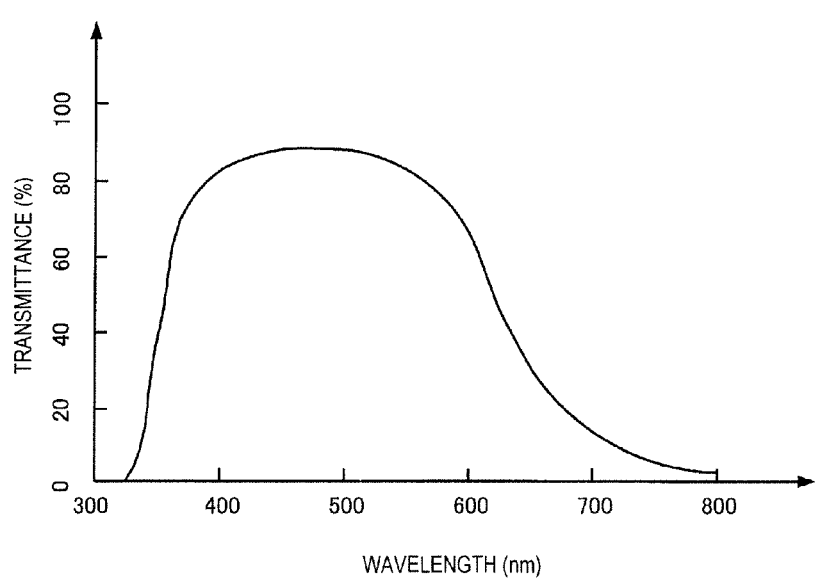
FIG. 9 is an example of transmission characteristics of light passing through the contact part.

FIG. 9 shows an example of transmission characteristics of light passing through the contact part 19. As shown in FIG. 9, the transmittance at the wavelength of light emitted by the light-emitting element 14 where the intensity is at the maximum shown, e.g., in FIG. 8 (i.e., 520 nm) is 50% or above.

There is no requirement for the substrate 11 shown in, e.g., FIG. 6B to be formed from a material that is transparent with respect to the wavelength of the first light R1 emitted by the light-emitting element 14; a normal printed circuit board may be used. The substrate 11 such as that shown in, e.g., FIG. 2A is formed from a material that is transparent with respect to the wavelength of the first light R1 emitted by the light-emitting element 14. As for an example of transmission characteristics of light passing through the substrate 11 itself, although not shown, transmittance of the substrate 11 with respect to the wavelength of 520 nm can be set to, e.g., 50% or above, as with the transmission characteristics shown in FIG. 9.

Figure 10A:
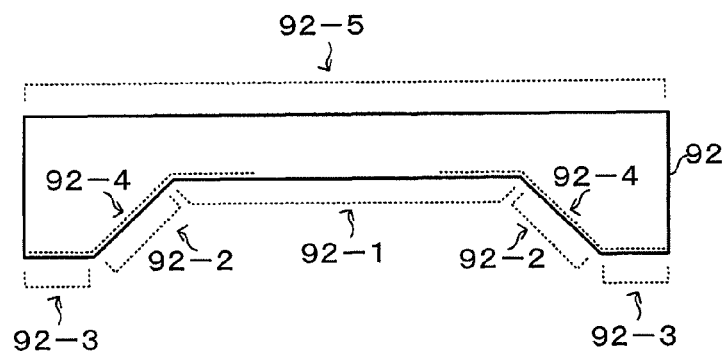
FIGS. 10A, 10B, and 10C are examples of a configuration of the support body (i.e., a first reflecting part)
Figure 10B:
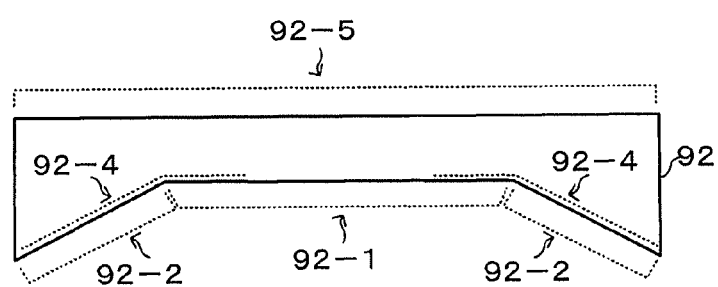
Figure 10C:
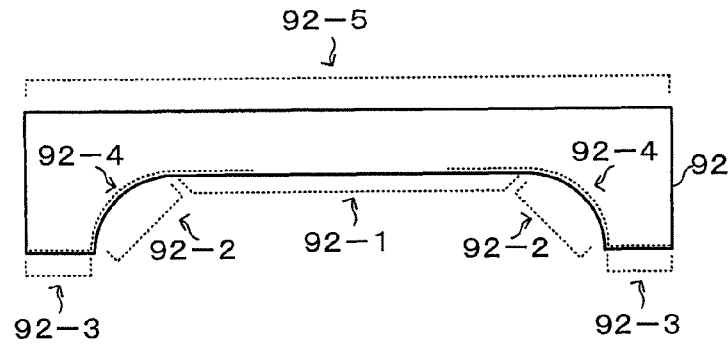

FIGS. 10A, 10B, and 10C are examples of a configuration of the support body 92 (i.e., the first reflecting part) shown in FIGS. 5A, 5B, 6A, and 6B. As shown in FIG. 10A, the support body 92 (i.e., the first reflecting part) may have a support part 92-1 for supporting the light-emitting element 14, and an inner wall surface 92-2 and a top surface 92-3 of a wall part surrounding a second light-emitting surface 14B of the light-emitting element 14. The light-emitting element 14 is not shown in FIGS. 10A through 10C. In the example shown in FIG. 10A, the support body 92 (i.e., the first reflecting part) can reflect the second light R2 on the inner wall surface 92-2 towards the detection site O (see FIG. 6A), the support body 92 having a first reflecting surface on the inner wall surface 92-2. The thickness of the support part 92-1 is, e.g., 50 μm to 1000 μm, and the thickness of the wall part (i.e., 92-3) is, e.g., 100 μm to 1000 μm.

In the example shown in FIG. 10A, the inner wall surface 92-2 has an inclined surface (92-2) which, with increasing distance in a width direction (i.e., a first direction) from a center of the support body 92 (i.e., the first reflecting part), inclines towards the detection site O in a height direction (i.e., a direction that is perpendicular to the first direction), in cross-section view. The inclined surface (92-2) in FIG. 10A is formed by, in cross-section view, an inclined plane, but may also be a curved surface shown in e.g., FIG. 10C, or a similar inclined surface. The inner wall surface 92-2 may also be formed as a plurality of inclined flat surfaces whose angle of inclination vary from one another, or by a curved surface having a plurality of curvatures. In an instance in which the inner wall surface 92-2 of the support body 92 (i.e., the first reflecting part) has an inclined surface, the inner wall surface 92-2 of the first reflecting part 92 is capable of reflecting the second light R2 towards the detection site O. In other words, the inclined surface on the inner wall surface 92-2 of the support body 92 (i.e., the first reflecting part) can be said to be the first reflecting surface for improving the directivity of the light-emitting element 14. In such an instance, the amount of light reaching the detection site O increases further. The top surface 92-3 shown in FIGS. 10A and 10C may be omitted as shown, e.g., in FIG. 10B. In FIGS. 10A through 10C, a range indicated by label 92-4 function as a mirror surface part.

Figure 11A:
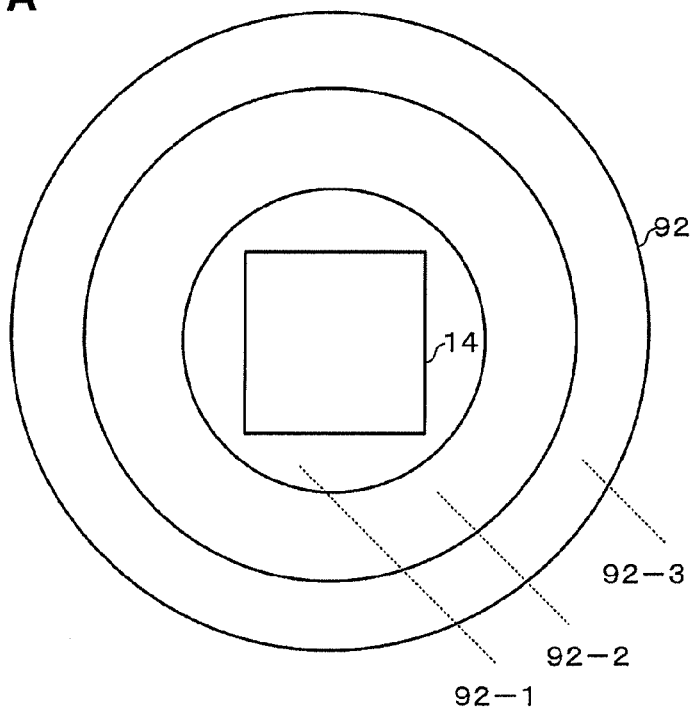
FIGS. 11A and 11B are examples of an outer appearance of the support body (i.e., the first reflecting part) and the light-emitting element.
Figure 11B:
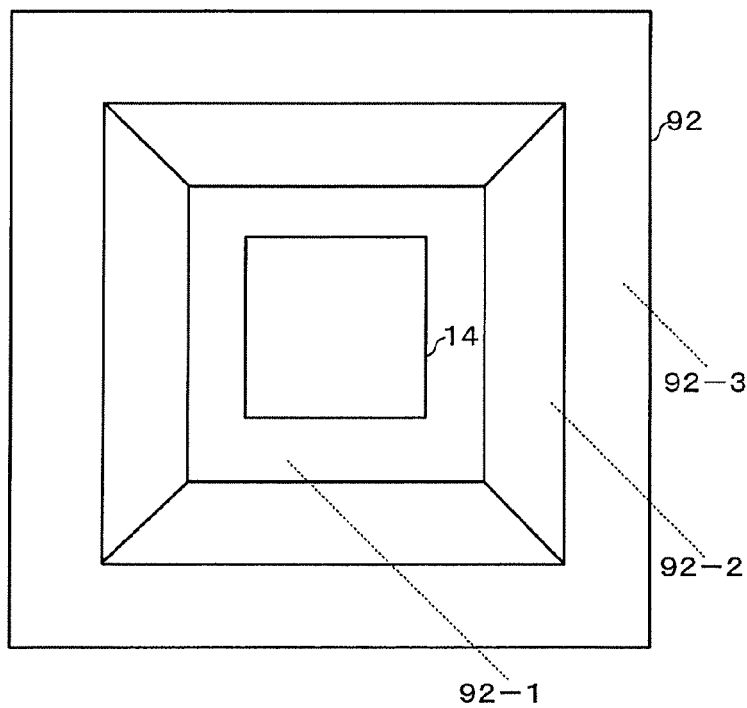

Each of FIGS. 11A and 11B shows an example of an outer appearance of the support body 92 (i.e., the first reflecting part) and the light-emitting element 14 of FIGS. 6A and 6B in plan view. In the example shown in FIG. 11A, with respect to the plan view (when viewed from, e.g., a side towards the detection site O shown in FIG. 6A), an outer circumference of the support body 92 (i.e., the first reflecting part) is circular, where the diameter of the circle is, e.g., 200 μm to 11,000 μm. In the example shown in FIG. 11A, the wall part (92-2) of the support body 92 (i.e., the first reflecting part) surrounds the light-emitting element 14 (see FIGS. 6A and 10A). The outer circumference of the support body 92 (i.e., the first reflecting part) may also be a quadrilateral (or specifically, a square) with respect to the plan view as shown, e.g., in FIG. 11B. Also, in the examples shown in FIGS. 11A and 11B, with respect to the plan view (when viewed from, e.g., a side towards the detection site O shown in FIG. 6A), the outer circumference of the light-emitting element 14 is a quadrilateral (or specifically, a square), where the length of one side of the square is, e.g., 100 μm to 10,000 μm. The outer circumference of the light-emitting element 14 may also be circular.

The support body 92 (i.e., the first reflecting part) is made of metal whose surface is polished to a mirror finish and thereby has a reflective structure (or specifically, a mirror reflection structure). The support body 92 (i.e., the first reflecting part) may also be formed from, e.g., a resin whose surface is polished to a mirror finish. Specifically, for example, a base metal forming a base of the support body 92 (i.e., the first reflecting part) is readied, and a surface of the base metal is then, e.g., subjected to plating. Alternatively, a mold (not shown) of the support body 92 (i.e., the first reflecting part) is filled with a thermoplastic resin, molding is performed, and a metal film, for example, is then deposited by vapor deposition on a surface of the mold.

In an instance in which the entirety of the support body 92 (i.e., the first reflecting part) is made from a metal, a support surface 92-5 of the support body 92 (i.e., the first reflecting part) is electroconductive. Also, in an instance in which the support body 92 (i.e., the first reflecting part) is formed from a resin, a metal film may be deposited by vapor deposition on the support surface 92-5, and the support surface 92-5 (i.e., the metal film) may be electroconductive.

In the examples shown in FIGS. 11A and 11B, with respect to the plan view (when viewed from, e.g., towards the detection site O shown in FIG. 6A), a region of the support body 92 (i.e., the first reflecting part) other than that directly supporting the light-emitting element 14 (i.e., the inner wall surface 92-2 and the top surface 92-3 of the wall part, and a part of the support part 92-1) is exposed. The exposed region is shown as a mirror surface part 92-4 in FIG. 10A. Although in the example shown in FIG. 10A, a dotted line representing the mirror surface part 92-4 is shown within the first reflecting part 92, the mirror surface part 92-4 is actually formed on a surface of the first reflecting part 92.

In the examples shown in FIGS. 10A, 10B, and 10C, the mirror surface part 92-4 preferably has a high reflectivity. The reflectivity of the mirror surface part 92-4 is, e.g., 80% to 90% or higher. It is possible for the mirror surface part 92-4 to be formed only on the inclined surface of the inner wall surface 92-2. In an instance in which the mirror surface part 92-4 is formed not only on the inclined surface of the inner wall surface 92-2 but also on the support part 92-1, the directivity of the light-emitting element 14 increases further.

In the example shown in FIG. 6A, the second light R2 travels into the test subject, and the reflected light R2' reflected at the detection site O travels towards the second reflecting part 18. Biological information (i.e., the pulse rate) is also reflected in the reflected light R2' reflected at the detection site O. In the example shown in FIG. 6A, the first light R1 is partially reflected at a surface SA of the test subject (i.e., skin surface). In an instance in which the detection site O is within the test subject, biological information (i.e., the pulse rate) is not reflected in reflected light R1" reflected at the surface SA of the test subject (i.e., directly reflected light).

The second reflecting part 18 is formed from, e.g., a resin whose surface (i.e., a reflecting surface on a side towards the light-receiving element 16) is polished to a mirror finish and thereby has a reflective structure (or specifically, a mirror reflection structure). In other words, the second reflecting part 18 is capable of causing mirror reflection of light without causing diffuse reflection of light. In an instance in which the second reflecting part 18 has a mirror reflection structure, the second reflecting part 18 is also capable of not causing the reflected light R1" produced by reflection of the first light R1 (i.e., directly reflected light; invalid light) to reflect towards the light-receiving element 16, the reflected light R1" having a reflection angle that is different from that of the reflected light R1' produced by reflection of the first light R1 (see FIG. 6A). In such an instance, the detection accuracy of the biological information detector (or in a broader sense, the optical device) is further increased. As shown in FIG. 6A, since the reflected light R1' produced by reflection of the first light R1 originates from the detection site O, which is within the test subject, the reflection angle of the reflected light R1' produced by reflection of the first light R1 (i.e., a reflection angle relative to a straight line perpendicular to the surface SA of the test subject) is generally small. Meanwhile, since the reflected light R1" produced by reflection of the first light R1 originates from the surface SA of the test subject, the reflection angle of the reflected light R1" produced by reflection of the first light R1 is generally large.

In FIG. 16 of Patent Citation 1, there is disclosed a reflecting part 131; and according to paragraphs [0046], [0059], and [0077] in Patent Citation 1, the reflecting part 131 has a diffuse reflection structure, and the reflectivity is increased to increase the efficiency of the light-receiving element 12. However, at the time of filing, it had not been recognized by those skilled in the art that in the reflecting part 131 according to Patent Citation 1, directly reflected light (or in a broader sense, noise) is also reflected towards the light-receiving element 12. In other words, the inventors recognized that reducing a noise component arising from the directly reflected light from a light reception signal increases the efficiency of the light-receiving element. Specifically, the inventors recognized that the detection accuracy of the biological information detector (or in a broader sense, the optical device) is further increased in an instance in which the second reflecting part 18 has a mirror reflection structure.

1.5 Third Configuration Example

Figure 12A:
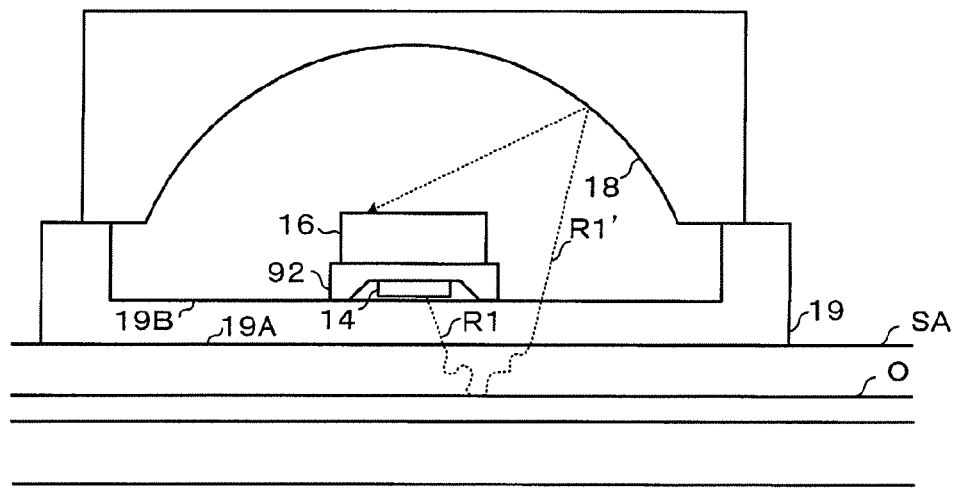
FIGS. 12A and 12B are other examples of the optical device according to the present embodiment.
Figure 12B:
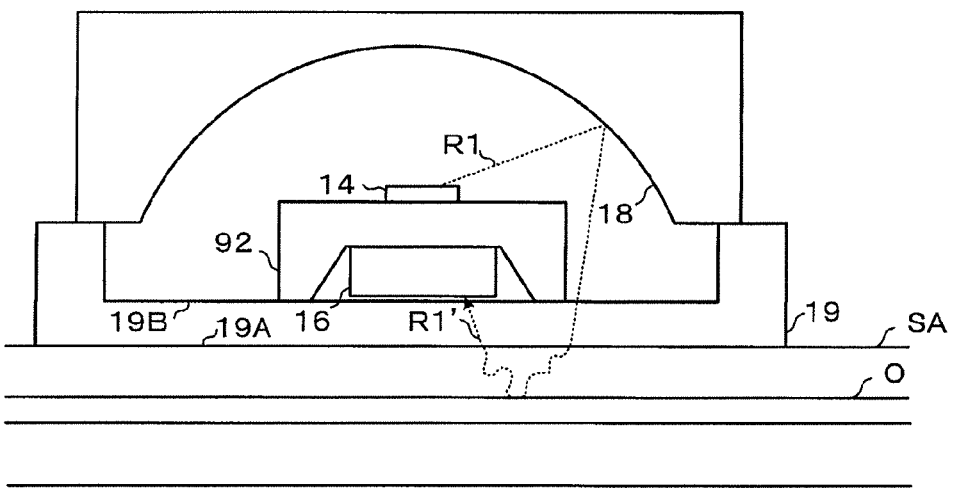

Each of FIGS. 12A and 12B shows another example of a configuration of the optical device according to the present embodiment. A cross-section view shown in FIG. 12A corresponds to the cross-section view shown in FIG. 1A, and a cross-section view shown in FIG. 12B corresponds to the cross-section view shown in FIG. 1B. Structures that are identical to those in the examples described above are identified with the same numerals, and a description of the structures is not provided. As shown in FIGS. 12A and 12B, the contact part 19 may have a depression, wherein the support body 92 is installed in the depression. Specifically, the shape of the contact part 19 shown, e.g., in FIG. 1A may be modified into the shape of the contact part 19 shown, e.g., in FIG. 2A.

In the examples shown in FIGS. 12A and 12B, the support body 92 is installed on the opposing surface 19B and made to support the first element. In the example shown in FIG. 12A, the light-receiving element 16, as the first element, is supported on the support body 92. In the example shown in FIG. 12B, the light-emitting element 14, as the first element, is supported on the support body 92. For example, in the example shown in FIG. 2B, there is a need for the substrate 11 (i.e., the first substrate portion 11-1) to be present, and there is a need to provide a space between the substrate 11 and the light-emitting element 14. In the examples shown in FIGS. 12A and 12B, a space of such description is not required, and the size of the optical device can be reduced.

As with the support body 92 shown in FIG. 6A, the support body 92 shown in FIG. 12A can also function as a reflecting part. As with the light-emitting element 14 shown in FIG. 6A, the light-emitting element 14 shown in FIG. 12A can be installed on the opposing surface 19B of the contact part 19, and the wirings 61, 62, 63, and 64 for at least one of the light-emitting element 14 and the light-receiving element 16 can be formed on the opposing surface 19B (see FIGS. 13A and 13B).

FIGS. 13A and 13B are schematic diagrams used to illustrate wiring for the light-emitting element 14. FIGS. 13A and 13B correspond to FIG. 12A. Structures that are identical to those in the examples described above are identified with the same numerals, and a description of the structures is not provided. In the example shown in FIGS. 13A and 13B, the wirings 63, 64 for the light-emitting element 14 are formed on the opposing surface 19B.

As shown in FIG. 13A, in an instance in which the wiring 64 (i.e., a second wiring for the light-emitting element 14) is disposed on the second surface 11B of the substrate 11, the wiring 64 disposed on the opposing surface 19B of the contact part 19 (i.e., a first wiring for the light-emitting element 14) is electrically connected to the wiring 64 disposed on the second surface 11B of the substrate 11 (i.e., the second wiring for the light-emitting element 14) with an electroconductive member interposed therebetween. In the example shown in FIG. 13A, the electroconductive member is, e.g., a spring 64-4. Using, e.g., gold plating on the spring makes the spring 64-4 electrically conductive. The electroconductive member may also be, e.g., an electroconductive rubber. In the example shown in FIG. 13B, the wiring 63 disposed on the opposing surface 19B of the contact part 19 (i.e., a first wiring for the light-emitting element 14) is electrically connected to the wiring 64 disposed on the second surface 11B of the substrate 11 (i.e., a second wiring for the light-emitting element 14) with an electroconductive member (e.g., a spring 63-4, an electroconductive rubber, or another member) interposed therebetween. In the example shown in FIGS. 13A and 13B, the light-emitting element 14 is installed on a surface of the wirings 64, 63 (i.e., the first wiring for the light-emitting element 14) via the bumps 64-2, 63-2.

Figure 14A:
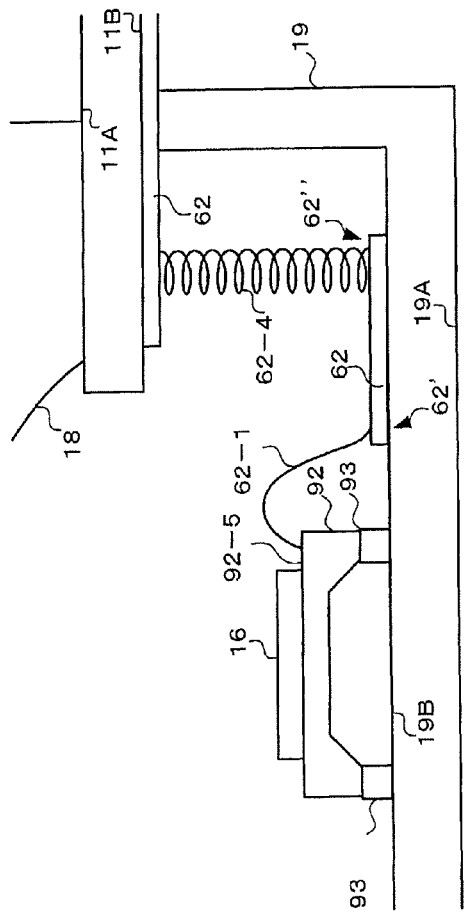
FIGS. 14A and 14B are schematic diagrams used to illustrate wiring for the light-receiving element.
Figure 14B:
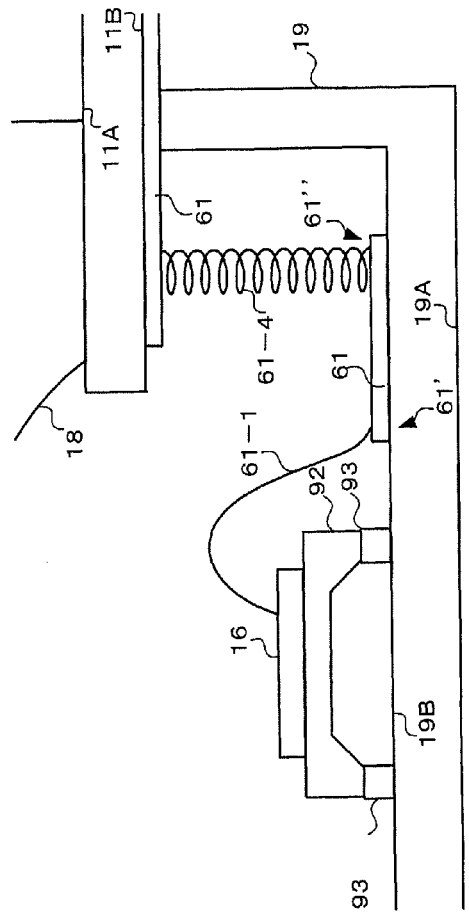

Although the light-receiving element 16 is not shown in the example shown in FIGS. 13A and 13B, the wirings 61, 62 for the light-receiving element 16 can be formed on the opposing surface 19B (FIGS. 14A and 14B).

FIGS. 14A and 14B are schematic diagrams used to illustrate wiring for the light-receiving element 16. FIGS. 14A and 14B correspond to FIG. 12A. Structures that are identical to those in the examples described above are identified with the same numerals, and a description of the structures is not provided. In the example shown in FIGS. 14A and 14B, the wirings 61, 62 for the light-receiving element 16 are formed on the opposing surface 19B. In the example shown in FIGS. 14A and 14B, the light-emitting element 14 is not shown. In the example shown in FIGS. 14A and 14B, the light-receiving element 16 is electrically connected to the wirings 62, 61 (or in a narrower sense, the connection pads 62', 61') formed on the opposing surface 19B with the bonding wires 62-1, 61-1 respectively interposed therebetween.

In an instance in which the support body 92 (i.e., the first reflecting part) is secured to the wiring 64 as shown in FIG. 6B, the thickness of the adhesive 93 may decrease. Therefore, in order to protect the wiring 64 (i.e., the wiring for the light-emitting element 14) (or in a broader sense, the opposing surface 19B), an insulating member 64-3 may be provided on the wiring 64 as shown in FIG. 13A. Also, in order to protect the wiring 63 (i.e., the wiring for the light-emitting element 14) (or in a broader sense, the opposing surface 19B), an insulating member 63-3 may be provided on the wiring 63 as shown in FIG. 13B. The support body 92 (i.e., the first reflecting part) is thus secured on the opposing surface 19B via the insulating members 63-3, 64-3. The insulating members 63-3, 64-3 can be formed from, e.g., a solder resist (or, in a broader sense, a resist).

An insulating member may also be provided on the wirings 61, 62. In an instance in which the contact part 19 does not have a depression, as shown, e.g., in FIG. 6B, there is no need for the springs 61-4, 62-4, 63-4, 64-4 in FIGS. 13A, 13B, 14A, and 14B to be necessarily provided. In an instance in which the contact part 19 is flat, as shown, e.g., in FIG. 6B, it is possible to provide an optical device (or in a narrower sense, a biological information detector) that can be readily assembled.

1.6 Example of Modification

Figure 15:
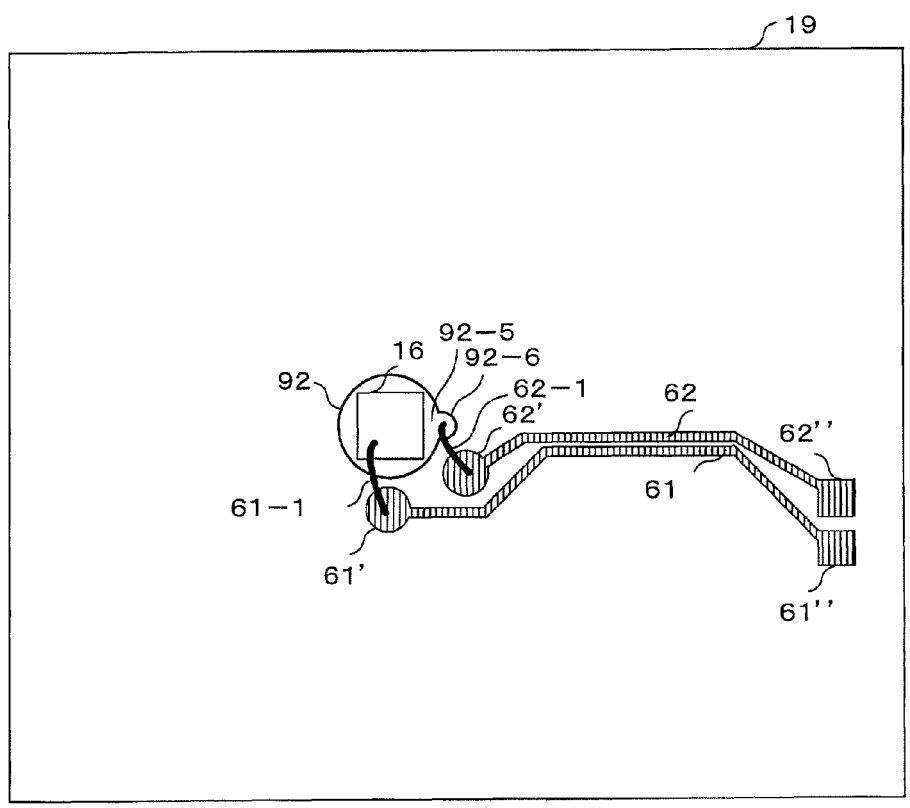
FIG. 15 is an example of a modification of the support body (i.e., the first reflecting part)

FIG. 15 shows an example of modification of the support body 92 shown in FIG. 7A. As shown in FIG. 15, the support body 92 may have an extended portion 92-6 for receiving the bonding wire 62-1. Increasing the size of the profile of the light-receiving element 16 in order to increase the efficiency of the light-receiving element 16 reduces the area of the support surface 92-5 for receiving the bonding wire 62-1. In such an instance, it may be difficult to connect the bonding wire 62-1 to the support surface 92-5, or the reliability of the bonding wire 62-1 connected to the support surface 92-5 may decrease. Also, increasing the size of the support body 92 increases the size of the light-blocking region. Providing the extended portion 92-6 makes it possible to prevent the area of the support surface 92-5 from being larger than necessary. Also, providing the extended portion 92-6 makes it possible to more readily connect the bonding wire 62-1 to the support surface 92-5 and increases the reliability of the bonding wire 62-1 connected to the support surface 92-5. The extended portion 92-6 shown in FIG. 15A can be applied to, e.g., the support body 92 shown in FIG. 6A or 14A.

2. Biological Information Measuring Device

Figures 16A, 16B:
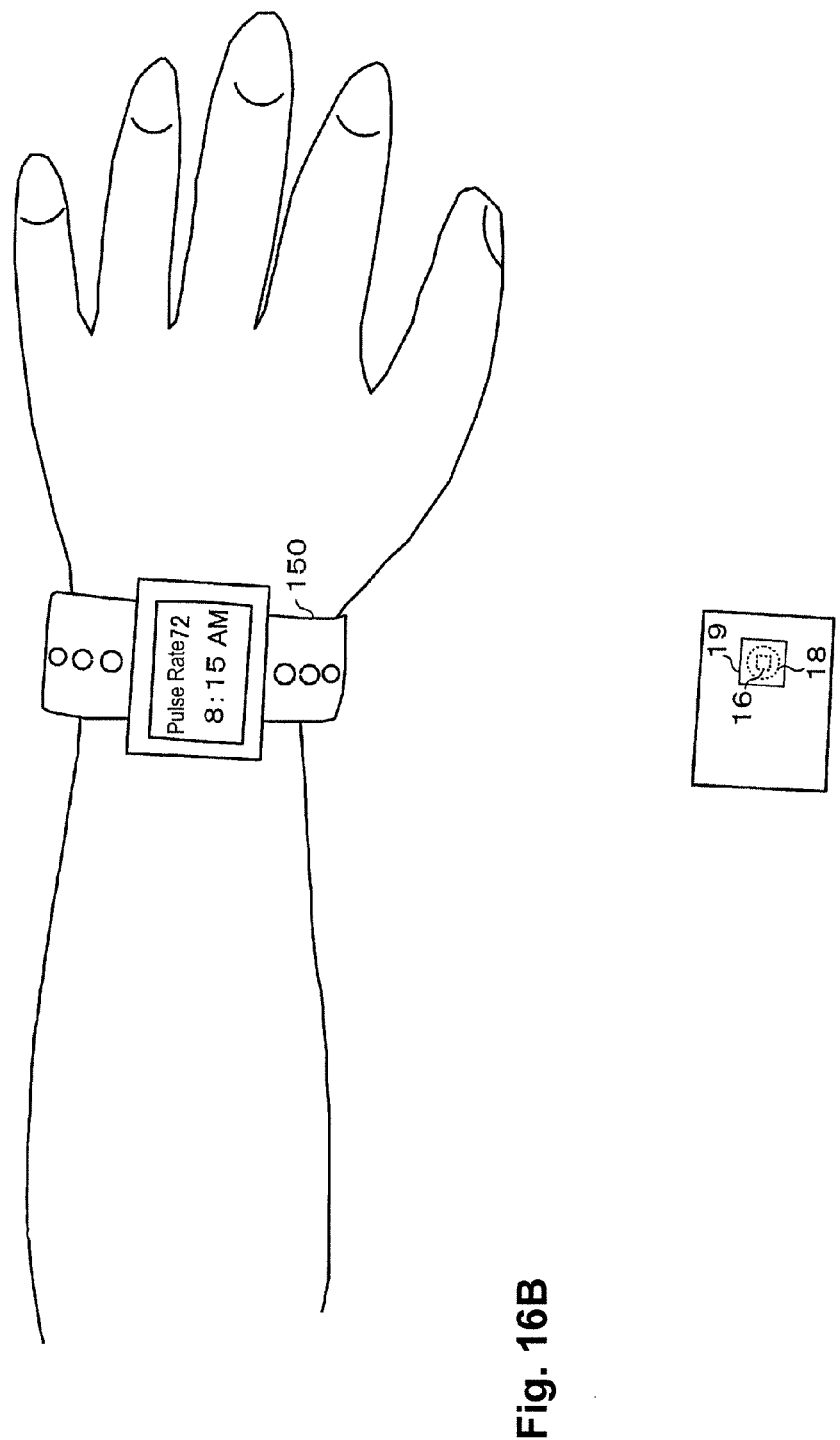
FIGS. 16A and 16B are an example of an outer appearance of a biological information measuring device including the biological information detector (or in a broader sense, the optical device)

FIGS. 16A and 16B are examples of the outer appearance of a biological information measuring device including the biological information detector (or in a broader sense, the optical device) such as that shown in FIGS. 1A, 6A, and other drawings. As shown in FIG. 16A, the biological information detector (or in a broader sense, the optical device) shown, e.g., in FIG. 1 may further comprise a wristband 150 capable of attaching the biological information detector to an arm (or in a narrower sense, a wrist) of the test subject (i.e., the user). In the example shown in FIG. 16A, the biological information is the pulse rate indicated by, e.g., "72." The biological information detector is installed in a wristwatch showing the time (e.g., "8:15 am"). As shown in FIG. 16B, an opening part is provided to a back cover of the wristwatch, and the contact part 19 shown, e.g., in FIG. 1 is exposed in the opening part. In the example shown in FIG. 16B, the second reflecting part 18 and the light-receiving element 16 are installed in a wristwatch. In the example shown in FIG. 16B, the support body 92 (i.e., the first reflecting part), the light-emitting element 14, the wristband 150, and other components are not shown.

Figure 17:
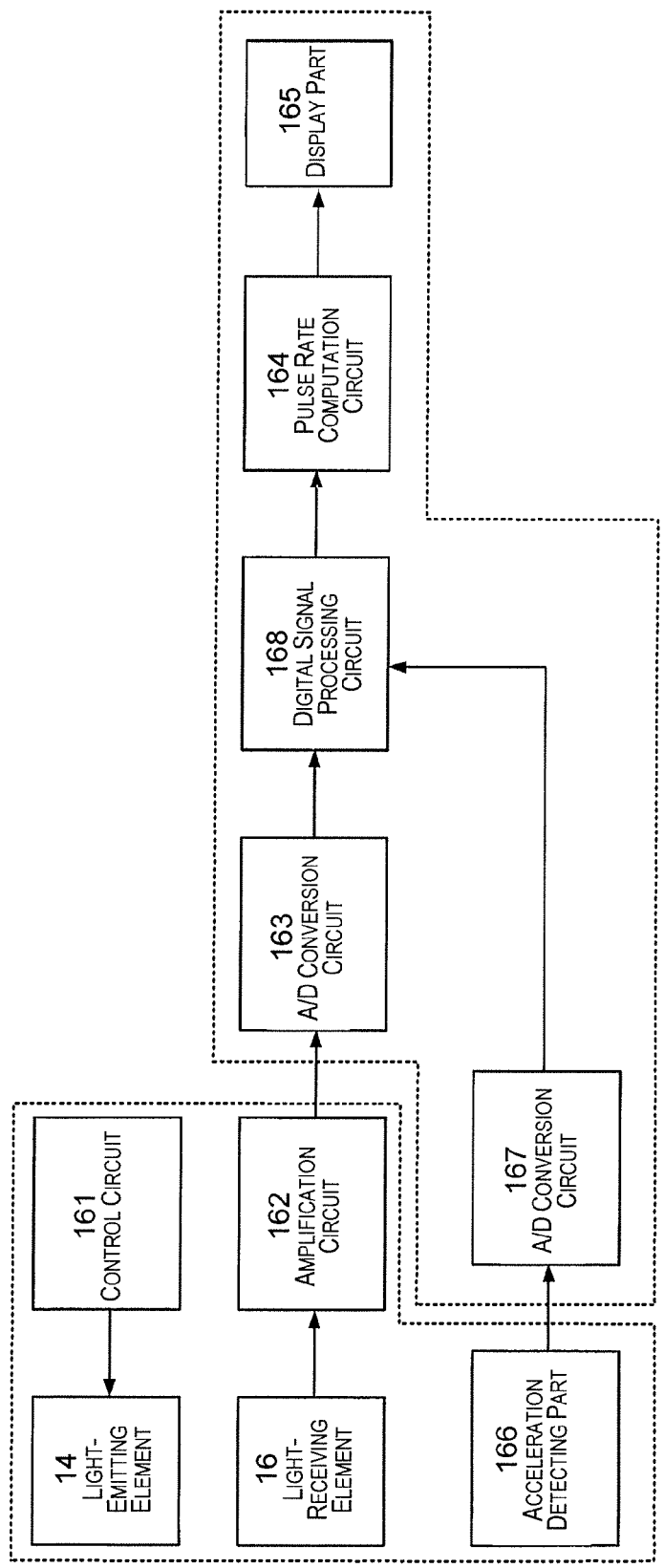
FIG. 17 is an example of a configuration of the biological information measuring device.

FIG. 17 is an example of a configuration of the biological information measuring device. The biological information measuring device includes the biological information detector as shown, e.g., in FIGS. 1A and 6A, and a biological information measuring part for measuring biological information from a light reception signal generated at the light-receiving element 16 of the biological information detector. As shown in FIG. 17, the biological information detector may have the light-emitting element 14, the light-receiving element 16, and a circuit 161 for controlling the light-emitting element 14. The biological information detector may further have a circuit 162 for amplifying the light reception signal from the light-receiving element 16. The biological information measuring part may have an A/D conversion circuit 163 for performing A/D conversion of the light reception signal from the light-receiving element 16, and a pulse rate computation circuit 164 for calculating the pulse rate. The biological information measuring part may further have a display part 165 for displaying the pulse rate.

The biological information detector may have an acceleration detecting part 166, and the biological information measuring part may further have an A/D conversion circuit 167 for performing A/D conversion of an acceleration signal from the acceleration detecting part 166 and a digital signal processing circuit 168 for processing a digital signal. The configuration of the biological information measuring device is not limited to that shown in FIG. 17. The pulse rate computation circuit 164 in FIG. 17 may be, e.g., an MPU (i.e., a micro processing unit) of an electronic device installed with the biological information detector.

The control circuit 161 in FIG. 17 drives the light-emitting element 14. The control circuit 161 is, e.g., a constant current circuit, delivers a predetermined voltage (e.g., 6 V) to the light-emitting element 14 via a protective resistance, and maintains a current flowing to the light-emitting element 14 at a predetermined value (e.g., 2 mA). The control circuit 161 is capable of driving the light-emitting element 14 in an intermittent manner (e.g., at 128 Hz) in order to reduce consumption current. The control circuit 161 is formed on, e.g., a motherboard, and wiring between the control circuit 161 and the light-emitting element 14 is formed, e.g., on the substrate 11 and the contact part 19 shown in FIGS. 6A and 6B.

The amplification circuit 162 shown in FIG. 17 is capable of removing a DC component from the light reception signal (i.e., an electrical current) generated in the light-receiving element 16, extracting only an AC component, amplifying the AC component, and generating an AC signal. The amplification circuit 162 removes the DC component at or below a predetermined wavelength using, e.g., a high-pass filter, and buffers the AC component using, e.g., an operational amplifier. The light reception signal contains a pulsating component and a body movement component. The amplification circuit 162 or the control circuit 161 is capable of feeding a power supply voltage for operating the light-receiving element 16 at, e.g., reverse bias to the light-receiving element 16. In an instance in which the light-emitting element 14 is intermittently driven, the power supply to the light-receiving element 16 is intermittently fed, and the AC component is intermittently amplified. The amplification circuit 162 is formed on, e.g., the motherboard, and wiring between the amplification circuit 162 and the light-receiving element 16 is formed on, e.g., the substrate 11 shown in FIGS. 6A and 6B. The amplification circuit 162 may also have an amplifier for amplifying the light reception signal at a stage prior to the high-pass filter. In an instance in which the amplification circuit 162 has an amplifier, the amplifier is formed, e.g., on the substrate 11.

The A/D conversion circuit 163 shown in FIG. 17 converts an AC signal generated in the amplification circuit 162 into a digital signal (i.e., a first digital signal). The acceleration detecting part 166 shown in FIG. 17 detects, e.g., acceleration in three axes (i.e., an x-axis, a y-axis, and a z-axis) and generates an acceleration signal. Movement of the body (i.e., the arm), and therefore movement of the biological information measuring device, are reflected in the acceleration signal. The A/D conversion circuit 167 shown in FIG. 17 converts the acceleration signal generated in the acceleration detecting part 166 into a digital signal (i.e., a second digital signal).

The digital signal processing circuit 168 shown in FIG. 17 uses the second digital signal to remove or reduce the body movement component in the first digital signal. The digital signal processing circuit 168 may be formed with, e.g., an FIR filter or another adaptive filter. The digital signal processing circuit 168 inputs the first digital signal and the second digital signal into the adaptive filter and generates a filter output signal from which noise has been removed or which has reduced noise.

The pulse rate computation circuit 164 shown in FIG. 13 uses e.g., fast Fourier transform (or in a broader sense, discrete Fourier transform) to perform a frequency analysis on the filter output signal. The pulse rate computation circuit 164 identifies a frequency that represents a pulsating component based on a result of the frequency analysis, and calculates a pulse rate.

2.2 Pulse Oximeter

A description will now be given for a pulse oximeter as another example of the biological information measuring device. A biological information detector (or in a broader sense, an optical device) that is installed in the pulse oximeter can be obtained using a configuration that is identical to that used in the above-described embodiment (i.e., the configuration shown in, e.g., FIG. 6A or FIG. 1A).

A description will now be given based on the configuration shown in FIG. 6A. The pulse oximeter (or in a broader sense, the biological information detector) comprises the light-emitting element 14 and the light-receiving element 16. The light-emitting element 14 emits, e.g., a red light and infrared light. Reflected light, produced by reflecting at the detection site O (e.g., a blood vessel), is measured using the light-receiving element 16. Red-light and infrared absorbance of haemoglobin in the blood differ depending on presence of a bond with oxygen. Therefore, the arterial oxygen saturation ($S_pO_2$) can be measured by measuring the reflected light at the light-receiving element 16 and analyzing the reflected light.

The configuration of the biological information measuring part (i.e., the A/D conversion circuit 163, the pulse rate computation circuit 164, the display part 165, the acceleration detecting part 166, the A/D conversion circuit 167, and the digital signal processing circuit 168) for use in a pulse rate monitor as shown in FIG. 17 can be used as a configuration of the biological information measuring part for use in the pulse oximeter. However, the pulse rate computation circuit 164 shown in FIG. 17 is replaced by an arterial oxygen saturation analysis circuit 164 in which a pulse rate computation circuit and an FFT or another approach is used.

Although a detailed description was made concerning the present embodiment as stated above, persons skilled in the art should be able to easily understand that various modifications can be made without substantially departing from the scope and effects of the invention. Accordingly, all of such examples of modifications are to be included in the scope of the invention. For example, terms stated at least once together with different terms having broader sense or identical sense in the specification or drawings may be replaced with those different terms in any and all locations of the specification or drawings.

What is claimed is:

1. An optical device comprising:
a contact part having a contact surface and an opposing surface, the contact surface adapted to come into contact with a test subject, the opposing surface being opposite the contact surface;
a support body installed on the opposing surface, the support body having a first surface and a second surface, the first surface facing the opposing surface and the second surface being opposite the first surface;
a first element supported by the support body and installed on the second surface; and
a second element disposed between the opposing surface and the support body,
one of the first element and the second element being a light-emitting element for emitting light towards a detection site in the test subject,
the other of the first element and the second element being a light-receiving element for receiving reflected light, the reflected light being light emitted by the light-emitting element and reflected at the detection site,
the first and second elements sandwiching a part of the support body, wherein the part of the support body comprises the first and second surfaces, the first surface directly faces the second element, and the second surface directly contacts the first element,
the contact part being formed from a material that is transparent with respect to a wavelength of the light emitted by the light-emitting element.

2. The optical device according to claim 1, wherein wiring for at least one of the first element and the second element is formed on the opposing surface.

3. The optical device according to claim 2, further comprising:
a reflecting part for reflecting the light emitted by the light-emitting element or the reflected light; and
a substrate, disposed between the support body and the reflecting part; wherein
the wiring is electrically connected to a wiring formed on the substrate.

4. The optical device according to claim 1, wherein the first element is the light-receiving element, and the second element is the light-emitting element.

5. The optical device according to claim 4, wherein the support body has an electroconductive support surface, and an electrode on a support-surface-side of the light-receiving element is electrically connected to the support surface.

6. The optical device according to claim 1, wherein the light emitted by the light-emitting element has a first light directed at the detection site and a second light directed in a direction other than that of the detection site, and the support body has a reflecting surface for reflecting the second light towards the detection site.

7. The optical device according to claim 4, wherein the light-emitting element is installed on the opposing surface.

8. A biological information detector comprising:
the optical device according to any of claim 1, wherein the reflected light has pulse rate information.

9. An optical device comprising:
a contact part having a contact surface and an opposing surface, the contact surface adapted to contact with a test subject, the opposing surface being opposite the contact surface;
a support body installed on the opposing surface, the support body having a first surface and a second surface, the first surface facing the opposing surface and the second surface being opposite the first surface;

a first element supported by the support body and installed on the second surface;

a second element disposed between the opposing surface and the support body;

one of the first element and the second element being a light-emitting element for emitting light towards a detection site in the test subject;

the other of the first element and the second element being a light-receiving element for receiving reflected light, the reflected light being light emitted by the light-emitting element and reflected at the detection site;

the support body being arranged between the first element and second element, wherein the first surface directly faces the second element, and the second surface directly contacts the first element; and the contact part being formed from a material that is transparent with respect to a wavelength of the light emitted by the light-emitting element.

10. The optical device according to claim 9, wherein the first element is the light-receiving element, and the second element is the light-emitting element.

11. The optical device according to claim 10, further comprising:

a reflecting part for reflecting the light emitted by the light-emitting element being arranged on the opposing surface.

12. An optical device comprising:

a contact part having a contact surface and an opposing surface, the contact surface adapted to contact with a test subject, the opposing surface being opposite the contact surface;

a support body installed on the opposing surface, the support body having a first surface and a second surface, the first surface facing the opposing surface and the second surface being opposite the first surface;

a first element supported by the support body and installed on the second surface;

a second element supported by the support body, wherein the first surface directly faces the second element, and the second surface directly contacts the first element, wherein the contact part being formed from a material that is transparent with respect to a wavelength of the light emitted by the light-emitting element.

13. The optical device according to claim 12, wherein wiring for at least one of the first element and the second element is formed on the opposing surface.

14. The optical device according to claim 12, wherein the first element is the light-receiving element, and the second element is the light-emitting element.

15. The optical device according to claim 14, wherein the support body has an electroconductive support surface, and an electrode on a support-surface-side of the light-receiving element is electrically connected to the support surface.

16. A biological information detector comprising: the optical device according to any of claim 12, wherein the reflected light has pulse rate information.

* * * * *